United States Patent
Lading et al.

(10) Patent No.: US 10,470,717 B2
(45) Date of Patent: Nov. 12, 2019

(54) PULSE VALIDATION

(71) Applicant: Capsule Technologies, Inc., San Diego, CA (US)

(72) Inventors: Lars Lading, Roskilde (DK); David Boettcher Baek, San Diego, CA (US)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 514 days.

(21) Appl. No.: 15/047,103

(22) Filed: Feb. 18, 2016

(65) Prior Publication Data

US 2017/0238878 A1    Aug. 24, 2017

(51) Int. Cl.
*A61B 5/00* (2006.01)
*A61B 5/024* (2006.01)

(52) U.S. Cl.
CPC ............ *A61B 5/7221* (2013.01); *A61B 5/024* (2013.01); *A61B 5/02438* (2013.01); *A61B 5/726* (2013.01); *A61B 5/7246* (2013.01)

(58) Field of Classification Search
CPC ... A61B 5/7221; A61B 5/726; A61B 5/02438; A61B 5/7246
USPC ....................................................... 600/500
See application file for complete search history.

(56) References Cited

U.S. PATENT DOCUMENTS

| | | | |
|---|---|---|---|
| 7,674,231 B2 | 3/2010 | McCombie et al. | |
| 8,506,498 B2 | 8/2013 | Sethi et al. | |
| 8,672,854 B2 | 3/2014 | McCombie et al. | |
| 2007/0055151 A1* | 3/2007 | Shertukde | A61B 5/02007 600/437 |
| 2010/0016738 A1 | 1/2010 | Addison et al. | |
| 2012/0123232 A1 | 5/2012 | Najarian et al. | |
| 2013/0006128 A1 | 1/2013 | Olde et al. | |
| 2013/0023776 A1 | 1/2013 | Olde et al. | |
| 2013/0066176 A1* | 3/2013 | Addison | A61B 5/7207 600/324 |
| 2013/0079657 A1 | 3/2013 | Ochs et al. | |
| 2013/0150766 A1 | 6/2013 | Olde et al. | |
| 2014/0073954 A1 | 3/2014 | Engelbrecht et al. | |
| 2014/0213862 A1 | 7/2014 | Addison et al. | |
| 2015/0025808 A1* | 1/2015 | Aguiar | A61B 5/201 702/19 |
| 2015/0149116 A1* | 5/2015 | Cho | G01G 9/00 702/173 |

(Continued)

OTHER PUBLICATIONS

International Search Report and Written Opinion—PCT/US2017/013901—ISA/EPO—dated May 9, 2017.

(Continued)

*Primary Examiner* — Jacqueline Cheng
*Assistant Examiner* — Tho Q Tran
(74) *Attorney, Agent, or Firm* — Kilpatrick Townsend & Stockton LLP

(57) ABSTRACT

Various embodiments identify valid arterial pulses of a subject. The method may include accessing one or more measured pulses from one or more arterial measurement sensors. The processor may identify one or more valid pulses from the one or more measured pulses based on a comparison of one or more pulse characteristics of the one or more measured pulses to one or more reference pulses. The one or more pulse characteristics are determined based on the one or more measured pulses and a wavelet transform. The wavelet transform is determined based on the one or more reference pulses.

30 Claims, 15 Drawing Sheets

(56) References Cited

U.S. PATENT DOCUMENTS

2018/0256057 A1* 9/2018 Khandoker .......... A61B 8/0866

OTHER PUBLICATIONS

Nair T., et al., "Methodology for Detection of QRS Pattern Using Secondary Wavelets", Aug. 2, 2014 (Aug. 2, 2014), XP055362803, Retrieved from the Internet: URL: https://arxiv.org/ftpjarxivjpapers/1408/1408.0452.pdf.

* cited by examiner

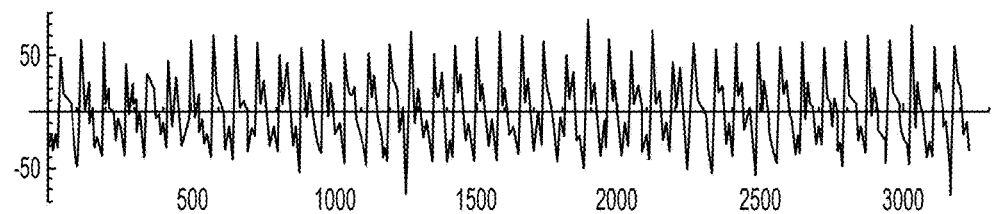
FIG. 3
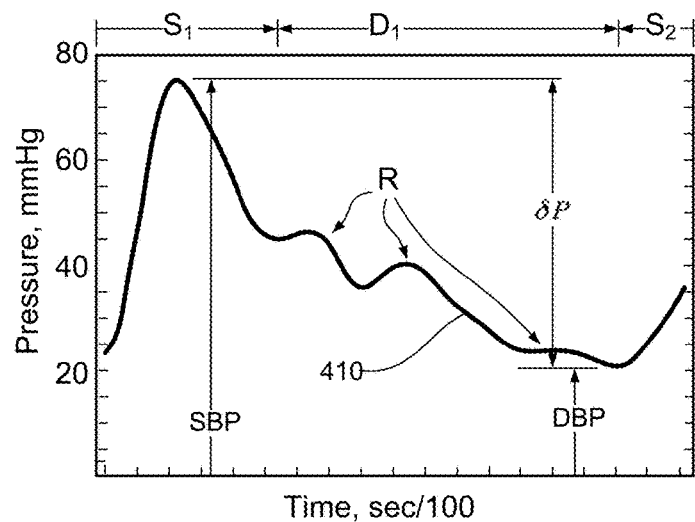
FIG. 4
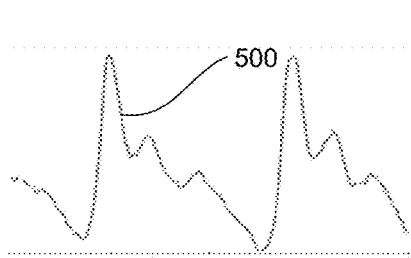 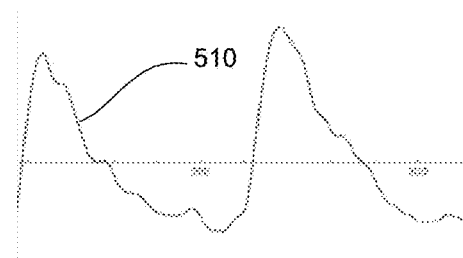
FIG. 5A    FIG. 5B

PULSE VALIDATION

BACKGROUND

Continuous monitoring of vital signs including blood pressure, may aid in detecting and diagnosing many conditions. Using continuous monitoring, a subject may be able to perform his or her normal everyday activities, such as work, sleep, and relaxation while vital signs are determined. In addition, to avoid influencing the measurements, the subject may have no perception of when measurements are performed.

Measuring characteristics used in determined vital signs and/or measuring vital signs may be perturbed by body movements, such as movements of limbs or movements associated with respiration. The perturbations are particularly pronounced when monitoring is performed under conditions in which the subject is allowed or encouraged to act freely. These movements may introduce artifacts that could perturb measurements used in determining a subject's vital signs. As a result, this may lead to the subject's vital signs being inaccurate.

SUMMARY

The method of the various embodiment may identify valid arterial pulses of a subject. Various embodiment may include accessing one or more measured pulses from one or more arterial measurement sensors. The one or more processors may identify one or more valid pulses from the one or more measured pulses based on a comparison of one or more pulse characteristics of the one or more measured pulses to one or more reference pulses. The one or more pulse characteristics are determined based on the one or more measured pulses and a wavelet transform. Wavelet transforms are determined based on the one or more reference pulses.

In one embodiment, the measuring device may identify valid arterial pulses of a subject. Various embodiment may include one or more arterial measurement sensors configured to measure arterial dynamics from an artery when positioned on a limb of a subject. The one or more processors coupled to the one or more arterial measurement sensors may be capable of accessing one or more measured pulses from the one or more arterial measurement sensors. The one or more processors may also be capable of identifying one or more valid pulses from the one or more measured pulses based on a comparison of one or more pulse characteristics of the one or more measured pulses to one or more reference pulses. The one or more pulse characteristics are determined based on the one or more measured pulses and a wavelet transform. The wavelet transform is determined based on the one or more reference pulses.

In one embodiment, the measuring device may identify valid arterial pulses of a subject. The measuring device may comprise means for accessing one or more measured pulses from the one or more arterial measurement sensors. The measuring device may also comprise means for identifying one or more valid pulses from the one or more measured pulses based on a comparison of one or more pulse characteristics of the one or more measured pulses to one or more reference pulses. The one or more pulse characteristics are determined based on the one or more measured pulses and a wavelet transform. The wavelet transform is determined based on the one or more reference pulses.

In one embodiment, the non-transitory computer-readable medium may contain instructions to identify valid arterial pulses of a subject. The non-transitory computer-readable medium may comprise at least one instruction to access one or more measured pulses from the one or more arterial measurement sensors. The non-transitory computer-readable medium may comprise at least one instruction to identify one or more valid pulses from the one or more measured pulses based on a comparison of one or more pulse characteristics of the one or more measured pulses to one or more reference pulses. The one or more pulse characteristics are determined based on the one or more measured pulses and a wavelet transform. The wavelet transform is determined based on the one or more reference pulses.

BRIEF DESCRIPTION OF THE DRAWING

The accompanying drawings, which are incorporated herein and constitute part of this specification, illustrate embodiments of the claims, and together with the general description given above and the detailed description given below, serve to explain the features of the claims.

FIG. 3 is a graph of the measurement signal according to various embodiments.

FIG. 4 is a graph of pressure versus time for a pulse pressure of a measured pulse and the start of a subsequent pulse.

FIG. 5A is a graph of a measured pulse for a thirty-two-year-old healthy male subject.

FIG. 5B is a graph of a measured pulse for a seventy-two-year-old male subject.

DETAILED DESCRIPTION

Figure 1A:
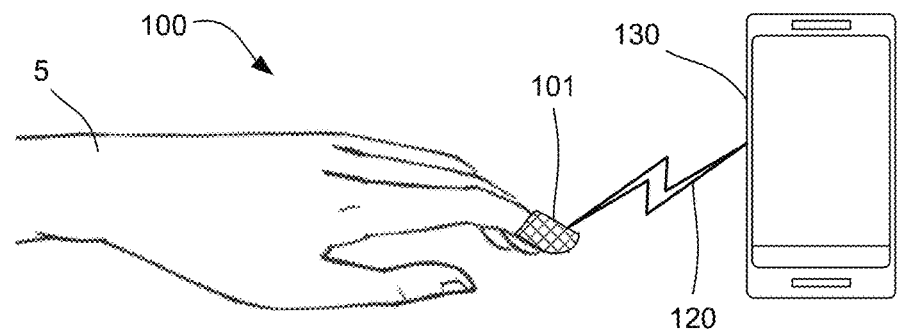
FIG. 1A is a schematic diagram of a device for identifying valid pulses from one or more measured pulses according to various embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments include methods, systems, and devices for identifying valid pulses measured from an artery in a limb of a subject without requiring a reference device (e.g., an inflatable cuff). In the various embodiments, pulses in arteries generated by the beating of the heart may be identified and selected as suitable for further processing in relation to cardiovascular properties. Various embodiment methods may include measuring a change in distension of the artery from a location on the limb without interfering with pulse pressure in the artery at the measurement location during a series of pulses. Various embodiment methods may determine a pulse rate and a pulse pressure from the change in distension. Various embodiments include a measuring device that provides an output (e.g., a measured quantity) for identifying valid pulses, as well as characteristics of pulse waveforms that may be used for diagnostics.

The terms "arterial pulse" or "pulse" are used interchangeably herein to refer to arterial dynamics caused by pulses of blood through the arterial system driven by contractions of the heart. A "reference pulse" may include one or more pulses used as a source of information or for comparison with one or more other pulses. One or more measured pulses may be normalized by substituting each measured pulse with a scaled version of the reference pulse. The scale of each substituted reference pulse may be based on a "peak normalized correlation," which is determined based on a ratio of a measured value from each measured pulse over a predetermined value from the reference pulse. The arterial dynamics may include repeated arterial changes, such as expansion of an artery measured as distension. In addition, arterial dynamics may include flow pulses or even pressure pulses. As used herein, the expression "pulse rate" refers to a ratio of the arterial dynamics over time, reflecting how frequently the heart beats (i.e., a heart rate).

The term "blood pressure" is used herein as a general term to refer to a pressure in the arterial system of the subject. A pulse pressure over a time period of at least one heart beat may be considered a measure of blood pressure, since pulse pressure reflects the difference between maximum and minimum pressures of a pulse. The pulses may be arterial distension pulses, flow pulses, and/or pressure pulses (e.g., obtained from a tonometer).

As used herein, the term "measuring device" refers to a physical apparatus for taking measurements of a biometric. In contrast, the terms "measurement sensor" or "sensor" generally refer to a device that responds to a physical stimulus (as heat, light, sound, pressure, magnetism, or a particular motion) and provides a corresponding output (as for measurement or operating a control) in the form of a measurement signal. A sensor may measure changes in position, size, and/or composition, such as within an organ or a portion of a body. The term "arterial measurement sensor" more specifically refers to a component of the measuring device that directly performs the measurement of arterial dynamics, such as a physical characteristic of an artery of the subject. For example, an arterial measurement sensor may detect and/or measure fluctuations in blood flow and/or the cross-sectional area of an artery or the local lumen of an artery. Physical characteristics of an artery, such as the cross-sectional area A, may be measured with an arterial measurement sensor. Such measurements may be used to measure changes in arterial properties. Thus, changes in an arterial cross-sectional area over a pulse, which represent distension of the artery, may be quantified by the difference between the maximum and minimum cross-sectional areas over the pulse. The measuring device may include one or more arterial measurement sensors and an electronic processing device for processing signals from the one or more arterial measurement sensors and/or communicating with external equipment. Some non-limiting examples of sensors that may be used with the various embodiments include ultrasound sensors, bioimpedance sensors (i.e. impedance plethysmogram (IPG)), photoplethysmographic (PPG) sensors, a magnetic resonance imaging (MRI) scanner, or any combination thereof.

Any of a wide variety of measuring devices may be used with the various embodiments. For example, a measuring device may be configured to be wearable, such as in the form of, or incorporated into, a patch, a finger sleeve, a wrist cuff, a finger ring, band of a wrist watch, back case of a wrist watch, and/or other form of apparel (i.e., clothing that includes an embodiment of a measuring device 101). However, the various embodiments may be used with measuring devices that are not worn by a subject, but are configured to place the sensor against the skin of the subject. For example, a measuring device may be incorporated into safety belts, steering wheels, armrests, seats and other structures in an automobile, train, airplane, or other vehicle, and configured so that the sensor(s) are able to take arterial measurements of a subject. As another example, a measuring device may be incorporated into smart furniture and configured so that the sensor(s) is in direct contact with a subject or in close proximity with the subject. As a further example, a measuring device may be incorporated into athletic equipment, such as helmets, racket handles, wrist or headbands, shoes, socks, handle bars, etc., and configured so that the sensor(s) are able to take arterial measurements a subject.

As used herein, the expression "non-interfering measuring device" refers to a measuring device that does not interfere with or perturb the normal bodily functions or at least does not perturb an artery being measured. A non-interfering measuring device may be used continuously over a long period (e.g. over 1-24 hours) so that sensor readings may be taken over a longer period. When the pressure is monitored over a longer period, changes in the arterial dynamics can be observed over time, which may provide important diagnostic information about the subject.

Various embodiments include methods, devices, and systems by which arterial pulses may be analyzed to identify valid or representative pulses suitable to be used in analyses to provide a reliable estimate of cardiovascular quantities, such as blood pressure. Observed measurement signals that may be used to infer vascular measurements may be validated in order to provide a more suitable and accurate measure of blood pressure, as well as other quantities related to the dynamics of the cardiovascular system.

FIG. 1A illustrates an example of a measuring device 101 configured to identify one or more valid pulses in an artery of a subject 5 that is suitable for use with various embodiments. In this example, a computing device 130, remote from the sleeve 110, may operate as a control unit and be wirelessly coupled 120 to the sleeve 110 for processing data. In one embodiment, the computing device 130, remote from the sleeve 110, may operate as a control unit and be coupled via one or more wires 120 or may be coupled via a combination of one or more wires and one or more wireless links to the sleeve 110 for processing data. In one embodiment, the computing device 130 may be included in the measuring device 101. The computing device 130 may be a smartphone, watch-phone, wearable, tablet, laptop, or other computer. The sleeve 110 may include its own processor and transceiver for communicating with the computing device 130. In this way, data processing may be performed in the control unit 140 operating as a computing device, the computing device 130, or a combination of both. In addition, the sleeve 110 may have a separate power source, such as by wire coupling to a nearby source of power (e.g., electrical outlet or battery).

The location of the non-interfering measuring device 101, the measurement location of the sensors, and the location of the measured artery may be within close proximity of one another. However, the measurement location does not necessarily have to be coincident with the location of the measurement device. For example, various embodiments may include an ultrasound-based, PPG, or IPG sensor, which performs the measurement on a particular location at a distance from the sensor itself.

Various types of sensors and measuring devices may be used to measure dimensional characteristics of an artery. Some examples of sensors and measuring devices include devices that employ technologies such as ultrasound, nuclear magnetic resonance, propagating electro-magnetic waves, optical sensing, and/or bioelectrical impedance. For example, ultrasound may be used to measure distension of an artery wall or flow velocity (e.g., a Doppler velocimetry, speckle displacement, transit-time, etc). Nuclear magnetic resonance may also be used to measure distension. Other types of sensors and measuring devices include devices capable of detecting a propagation property of electromagnetic waves. In addition, optical instruments may be used to detect and measure arterial distension (e.g. photoplethysmography) and/or flow velocity. As described above, bioelectrical impedance may be measured, particularly in applications in which distension may be detected from the bioelectrical impedance variations. Additional devices suitable for measuring dimensional characteristics of an artery may be used in accordance with various embodiments.

Figure 1B:
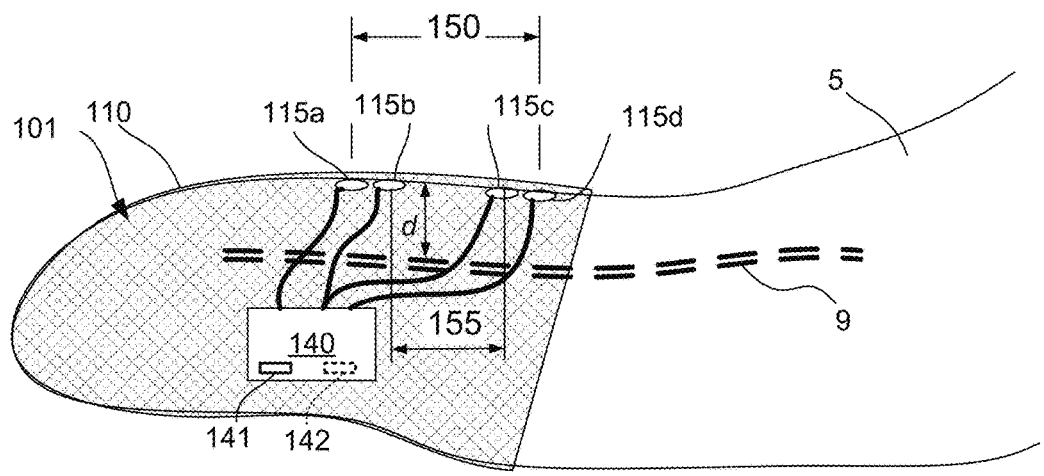
FIG. 1B is a schematic diagram of a device for identifying valid pulse measurements of a subject according to various embodiments.

FIG. 1B illustrates an example of a measuring device 101 configured to measure one or more valid pulses from an artery 9 in a limb of a subject 5 that is suitable for use with various embodiments. The measuring device 101 may be placed at a particular location on the subject 5 being measured (i.e., a select portion of the subject's body). For example, the measuring device 101 may include a sleeve 110, formed as a unitary structure that wraps partially or completely around a limb of the subject 5 (e.g., a subject's fingertip). In another example, the measuring device 101 may include sets of individual patches (each including one or more sensors) that are separated from one another. The sleeve 110 may be formed as an elastic band that incorporates a patch or patches with electrodes and a pouch or 'pocket' for holding electronics, such as a control unit 140.

In one embodiment, the sleeve 110 may also be a tightening band, such as an inflatable cuff, that may provide a counter pressure. In this case, the counter pressure may cause the measuring device 101 to be an interfering device.

In another embodiment, the sleeve 110 may be sized to ensure relatively low levels of counter pressure (i.e., inwardly from a surface of the skin) to ensure the underlying artery is not perturbed, i.e. non-interfering. In another example, the sleeve 110 need not impart any meaningful counter pressure, other than enough to ensure the one or more sensors 115 stay in engagement with or in close proximity with the subject's skin. If a constant counter pressure is applied, that constant counter pressure may be considered "a low level" as long as the counter pressure is well below a diastolic pressure (e.g., ≤~40 mmHg) of the subject. The counter pressure may be below 40 mmHg and may preferably be closer to 25 mmHg, which is far more comfortable to the subject. Such a minor constant counter pressure, which may be comparable to the pressure applied by compression stockings, will generally be lower than the pressure applied by an inflatable cuff-type blood pressure device (~200 mmHg). In addition, the application of the minor constant counter pressure may stabilize the veins without hampering a return blood flow. In this particular case, the measuring device 101 may be a non-interfering device.

The measuring device 101 may include one or more sensors 115. The one or more sensors 115 may be integrated into the sleeve 110, may be separate from the sleeve or any combination thereof. The one or more sensors 115 may include sensor processing, a sensor package or any combination thereof. In one embodiment, the one or more sensors 115 may include one or more electrodes. The sensors may be integrated into the inside surface of the sleeve 110 (i.e., configured to face the subject's skin when worn thereon) that presses against the skin or bring the one or more sensors 115 in close proximity with the skin. In some embodiments, a firm and even engagement between the skin and the sensor may be desirable. In another embodiment, the one or more sensors 115 may be integrated into one or more patches.

In one embodiment, the one or more sensors 115 may measure one or more parameters using bioelectric impedance, and the control unit 140 may be coupled to the electrodes for processing data. A first set of sensors may include a first inner detection sensor 115b and a first outer excitation sensor 115a. A second set of sensors may include a second inner detection sensor 115d and a second outer excitation sensor 115c.

The sensors 115a, 115b, 115c, 115d may be positioned on a portion of skin of the limb of the subject 5. In one embodiment, the sensors 115a-115d may each be separate sensors, electrodes as part of one or more sensors (e.g. sensors 115a-115d may be electrodes that make up a single sensor), or any combination thereof.

In one example, sensors 115a-115d are each electrodes that are part of one or more sensors. The sensors 115a and 115d (i.e. "outer excitation sensors") are electrodes that are used for excitation; whereas, 115b and 115c (i.e. "inner detection sensors") are electrodes that detect a response. The second set of two outer excitation sensors 115a, 115d may be placed with an outer separation distance 150 between the sensors somewhat larger than the depth d at which the artery 9 is embedded in the limb. This may be enable the electric field line to penetrate to a depth equal to or larger than the depth at which the artery is located. At the measurement area, a depth d may be less than 0.5 cm, but the separation may be considerably larger, only confined by the length of the limb. For example, the separation 150 may be between and including the depth d and the length of the limb. The first set of two inner detection sensors 115b, 115c may be placed with an inner separation distance 155, which is less than the outer separation distance 150 and disposed between the two outer excitation sensors 115a, 115d. The inner separation distance 155 may be approximately equal to half the depth d of the artery or greater. At the measurement area, the inner separation distance 155 may be from 1-2 mm to several centimeters. For example, in the case of a bioimpedence sensor where 115a-115d are electrodes, the inner separation distance 155 may be approximately 0.75 cm and the outer separation distance 150 may be approximately 1.5 cm. In another example, the outer excitation sensors and the inner detection sensors may swap places (i.e. the outer excitation sensors may be in closer proximity compared to the inner detection sensors)

A measuring device 101 may include a control unit 140, which may register and/or process outputs from the sensors 115a, 115b, 115c, 115d. Values from sensor measurements may be stored in optionally provided memory 141. Alternatively, external memory may be operatively coupled to the processor 142, directly or indirectly through the control unit 140. The control unit 140 may regulate and/or control the timing and/or output levels of the sensors 115a, 115b, 115c, 115d. The control unit 140 may also regulate and/or control the timing and/or pressure levels applied by the sleeve 110. The control unit 140 may include one or more processors 142 configured to make intermediate and/or final calculations and determinations regarding measurements. While the control unit 140 is illustrated as a single unit, multiple control units may be provided. Although connections 123 are illustrated as wired connections, the control unit 140 may include one or more wireless connections, such as using one or more wireless transceivers and antennas. Additionally, the control unit 140 may include a combination of wired connections 123 and wireless connections 123.

Figure 2:
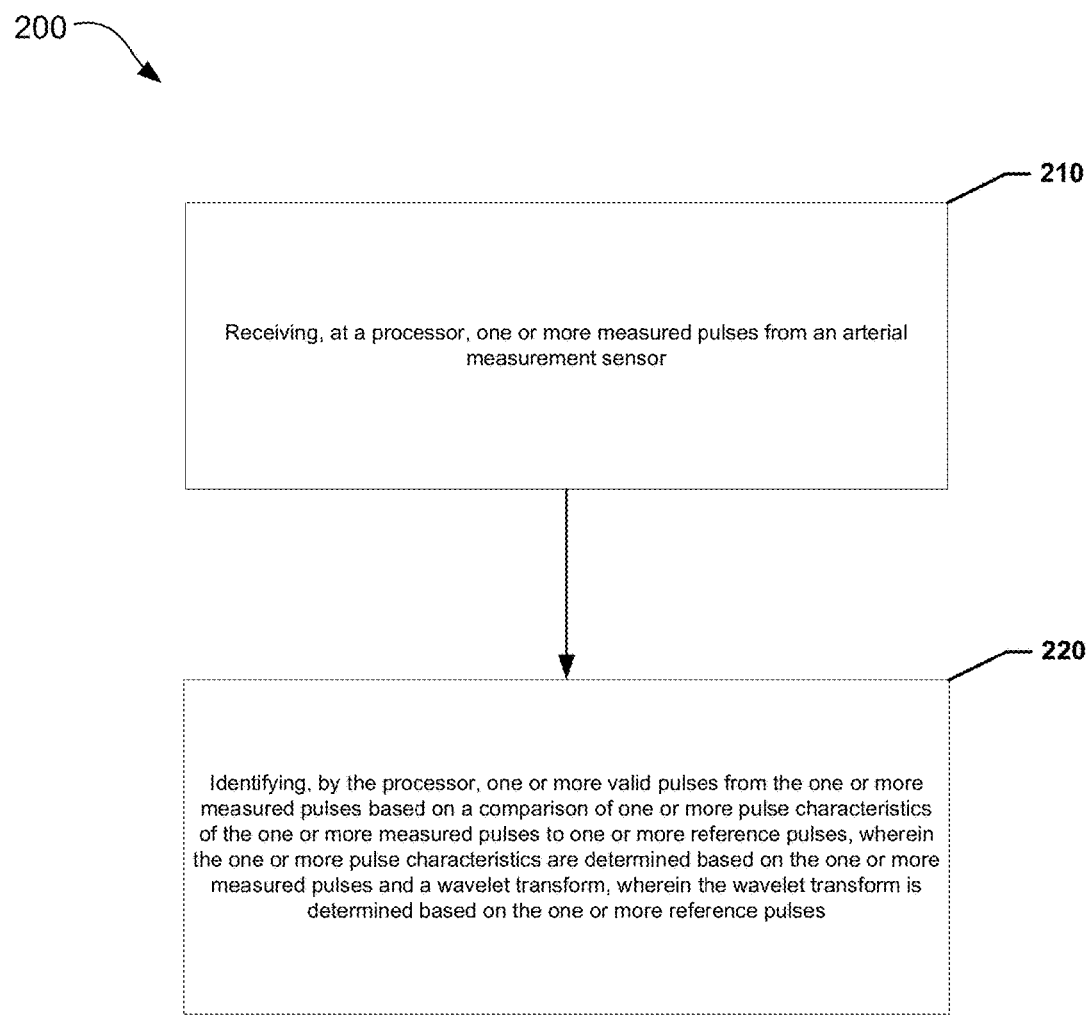
FIG. 2 is a process flow diagram illustrating an embodiment method for identifying valid measurements according to various embodiments.

FIG. 2 illustrates a method 200 of identifying valid pulses within measurement signals obtained by an arterial pulse measuring device, positioned on a limb of a subject, and performing measurements of arterial dynamics according to various embodiments. By identifying valid pulses within the measurement signals, the method 200 enables selection of particular portions of the measurement signals that are suitable for processing using various analysis methods for determining a subject's vital signs, such as blood pressure, and other physiological parameters. The various operations of the method 200 may be performed by a measuring device, including one or more sensor(s) and a control unit or other computing device and/or processor (referred to for simplicity as a "processor") in communication with the one or more sensors.

In block 210, the one or more processors may access one or more measured pulses from one or more arterial measurement sensors measuring parameters related to pressure within an artery of a subject. The one or more arterial measurement sensors may be any type of sensor that can measure physiological changes that characterize pressure, changes in pressure, and/or blood flow within an artery, some examples of which include pressure sensors (e.g., a tonometer), optical (e.g., photoplethysmographic) sensors, ultrasound sensors, bioimpedance sensors, or any combination thereof. For example, one or more measured pulses produced by the one or more arterial measurement sensors may reflect the diameter or change in diameter (referred to as "distension") measurements of an artery, because the diameter/distension of an artery will vary in response to changes in pressure within the artery that occur with each pulse. In one embodiment, the one or more processors may receive the one or more measured pulses from the one or more arterial measurement sensors directly or indirectly, such as from memory or through one or more intermediate devices. The one or more arterial measurement sensors may be an interfering (e.g., a tonometer) sensor in which a counter pressure is applied to the subject or a non-interfering sensor that applies limited or no counter pressure to the subject.

In one embodiment, the one or more arterial measurement sensors may generate one or more measured pulses.

As an example, FIG. 3 shows a graph of measurement signals from one or more arterial measurement sensors representing changes in distension of an artery of a subject over time. The changes in distension are shown comparing pressure as obtained from distension (i.e., the vertical axis, measured in mmHg) over time (i.e., the horizontal axis, measured in sec/100). Such changes in distension of an artery represent cardiovascular dynamics of the subject that may be correlated with a heart pulse rate.

The measurement signals may compromise one or more measured pulses. As an example, FIG. 4 is a graph of a measured pulse 410, showing the changes in pressure (i.e., the vertical axis, measured in mmHg) over time (i.e., the horizontal axis, measured in sec/100). The measured pulse 21 is an example of a measured pressure pulse that occurs after each contraction of the left heart ventricle illustrating some general features. Pulses are considered to have three parts. A first part, referred to as the systolic phase $S_1$, reflects the immediate rise of the pressure as a consequence of the ejection of blood from the heart, as part of a contraction thereof, and includes the peak of the pulse.

A second part, referred to as the diastolic phase $D_1$, reflects the fall of the pressure after the systolic phase. The diastolic phase is generally characterized by an exponentially decaying pressure. The exponential decay asymptotically approaches a value given by arterial and venous properties, but is redirected before doing so upon the occurrence of the subsequent pulse, which starts the next pulse's systolic phase $S_2$.

The exponential decay may be caused by the arterial system being connected with the veins through capillary network with a high fluid-flow resistivity and the veins being much more elastic than the arteries. Thus, the venous system essentially behaves like a capacitor, which has a capacitance much larger than that of the arterial system. Propagation effects may play an insignificant role for the decay since a time-constant of the decay may be much larger than the pulse propagation time through the arterial system.

The measured pulse 410 also includes reflections R, which form oscillations considered the third part, that result from discontinuities in the arterial system, such as bifurcations or diameter changes. The reflections R may vary among subjects and tend to be more pronounced in younger subjects and virtually non-existent in older subjects. For example, FIG. 5A is a graph of a reference pulse 500 modeled for a thirty-two-year old healthy male subject, which includes reflections. In contrast, FIG. 5B is a graph of a reference pulse 510 modeled for a seventy-two-year old male subject that basically does not include reflections in the diastolic part of the pulse. Oscillations may also be caused by interference between different arteries or caused by perturbations from other tissues.

In block 220, the one or more processors may identify valid pulses from the one or more measured pulses based on a comparison of one or more pulse characteristics of the one or more measured pulses to one or more reference pulses, wherein the one or more pulse characteristics are determined based on the one or more measured pulses and a wavelet transform, wherein the wavelet transform is determined based on the one or more reference pulses.

In one embodiment, the one or more measured pulses from the measurement signal are filtered based on the wavelet transform. Applying a wavelet transform to the measurement signals outputs pulses and/or indicates which pulses from the measurement signals are consistent with the wavelet, and rejects pulses and/or indicates which pulses from the measurement signals have a pressure-versus time profile inconsistent with typical or average pulses.

In one embodiment, the filter may be based on a reference pulse. In one example, the reference pulse may be used to determine the tailored mother wavelet. The reference pulse may be based on a generic or default waveform, a waveform customized to include characteristics predicted for the subject being measured, previously validated arterial pulses, previous arterial pulses, or any combination thereof. Previously validated arterial pulses may be based on prior reference data specific to the subject being measured, such as an average of the previously validated arterial pulses of the subject.

The reference pulse may be based on a model pulse through a calculation of the stroke volume versus time and a model for the propagation of the pulse through the arterial system. For example, a transmission line model may be used to determine a reference pulse that accommodates for time delay and changes of pulse shape as a consequence of the pulse propagation (e.g., propagation may cause a pulse shape to include sharp features, such as spikes). However, since the time scale of a pulse is generally large compared to the propagation time from the heart to the limb on which a measurement is performed, transmission line propagation may be neglected except for the steep on-set of the systole when modeling the reference pulse. From experimentally observed pulses, a simple third order response function may be used to represent most pulse shapes, which also takes pulse reflections into account. In addition, nonlinear effects may be considered in any reference pulse model.

The reference pulse may reflect some essential pulse properties, such as a generally asymmetric shape with an initial peaking during the systolic phase (e.g., $S_1$) and an exponential decay during the diastolic phase (e.g., $D_1$). The reference pulse may additionally be characterized by a peak occurring at a time corresponding to about a third of a total pulse length. In addition, an initial value uses for each pulse may be equal to an end value of a previous pulse. Similarly, an end value for each pulse may be determined based on the pulse amplitude at the onset of a subsequent pulse. The reference pulse may be designed to represent the most likely shape of a pulse, which may be reflected by a predetermined mathematical model. In addition, the reference pulse may be customized to accommodate specific characteristics associated with the subject being measured.

In one embodiment, the one or more reference pulses may be determined based on a subject's state. In one embodiment, the one or more reference pulses may be selected based on a subject's state. The measuring device 101 and/or a different device may determine a subject's state. In one embodiment, the measuring device 101 may determine a subject's movement state. For example, the measuring device 101 may determine if the subject's state is exercising, sitting/low movement, sleeping.

In one embodiment, the subject's state may be the subject's emotional state. For example, the measuring device 101 may determine if the subject is angry, depressed, sad, happy, stressed, etc.

In one embodiment, the subject's state may be a specific stage of the movement state or emotional state. For example, the subject's state may be a sleep stage (i.e. Stage 1, Stage 2, Stage 3, Stage 4, Rapid Eye Movement Stage).

In one embodiment, the subject's state may be based on the subject's movement state, subject's emotional state or any combination thereof.

In one embodiment, the one or more reference pulses may be associated with a particular subject state. For example, there may be one set of reference pulses associated with a subject exercising; whereas, a second set of reference pulses may be associated with a subject being asleep.

In one embodiment, one or more pulse characteristics are determined for the one or more measured pulses. The one or more pulse characteristics may comprise one or more pulse lengths, one or more pulse shapes, one or more amplitudes, one or more pulse locations or any combination thereof. In one embodiment, there may be one or more pulse characteristics for each measured pulse. For example, a measured pulse may have one or more pulse lengths, one or more amplitudes and one or more pulse shapes. It is important to note, that traditional blood pressure devices do not record the pulse characteristics such as pulse shape of the subject, so those device would be unable to perform subject specific pulse validation by utilizing pulse characteristics.

In one embodiment, the one or more processors may compare the one or more pulse characteristics of the one or more measured pulses to the one or more reference pulses. In one embodiment, the one or more processors may determine one or more peak normalized correlations of the one or more measured pulses based on the one or more pulse characteristics and the one or more reference pulses. For example, the one or more reference pulses may be compared to the one or more pulses locations.

In another example, the one or more reference pulses may be compared to the one or more pulse shapes and the one or more amplitudes. In one embodiment, the one or more reference pulses may be compared against each pulse characteristic separately. For example, the one or more reference pulse may be compared against the one or more pulse shapes and then may be compared against the one or more amplitudes. In one embodiment, the one or more pulse characteristics may be combined and then compared to the one or more reference pulses. For example, the one or more pulse shapes and the one or more amplitudes may be combined and then compared to the one or more reference pulses.

In one embodiment, the one or more processors may then identify as valid pulses those pulses among the one or more measured pulses whose one or more pulse characteristics that closely correlate to the one or more reference pulses. For example, valid pulses may be those one or more measured pulses that deviate from the reference pulse by no more than a predetermined correlation coefficient or maximum deviation. Thus, the one or more processors may determine the normalized correlation of the one or more pulse characteristics compared to the one or more reference pulses and identify one or more valid pulses from the one or more measured pulses where the normalized correlation meets or exceeds one or more correlation thresholds. Pulses not meeting the correlation threshold may be rejected, discarded, or indicated as unreliable or unrepresentative.

In one embodiment, the one or more processors may use the identified valid pulses to determine one or more vital sign measurements. For example, the valid pulses may be used to determine a subject's vital signs such as blood pressure, heart rate, respiratory rate, oxygen saturation, etc. By identifying valid pulses, it enables more accurate vital sign estimates and/or measurements, and allows the one or more processors to more easily separate noise/movement from valid pulses. For example, without identifying valid pulses various pulses may be misidentified which may lead to a higher heart rate estimation, erroneous blood pressure estimates, etc. In another example, some pulses may be misidentified as movements of a user's which may lead to lower heart rate estimation.

In one embodiment, the one or more processors may output the identified valid pulses to a local display, store the identified valid pulses in memory, and/or transmit the identified valid pulses to a remote computing device.

Figure 6:
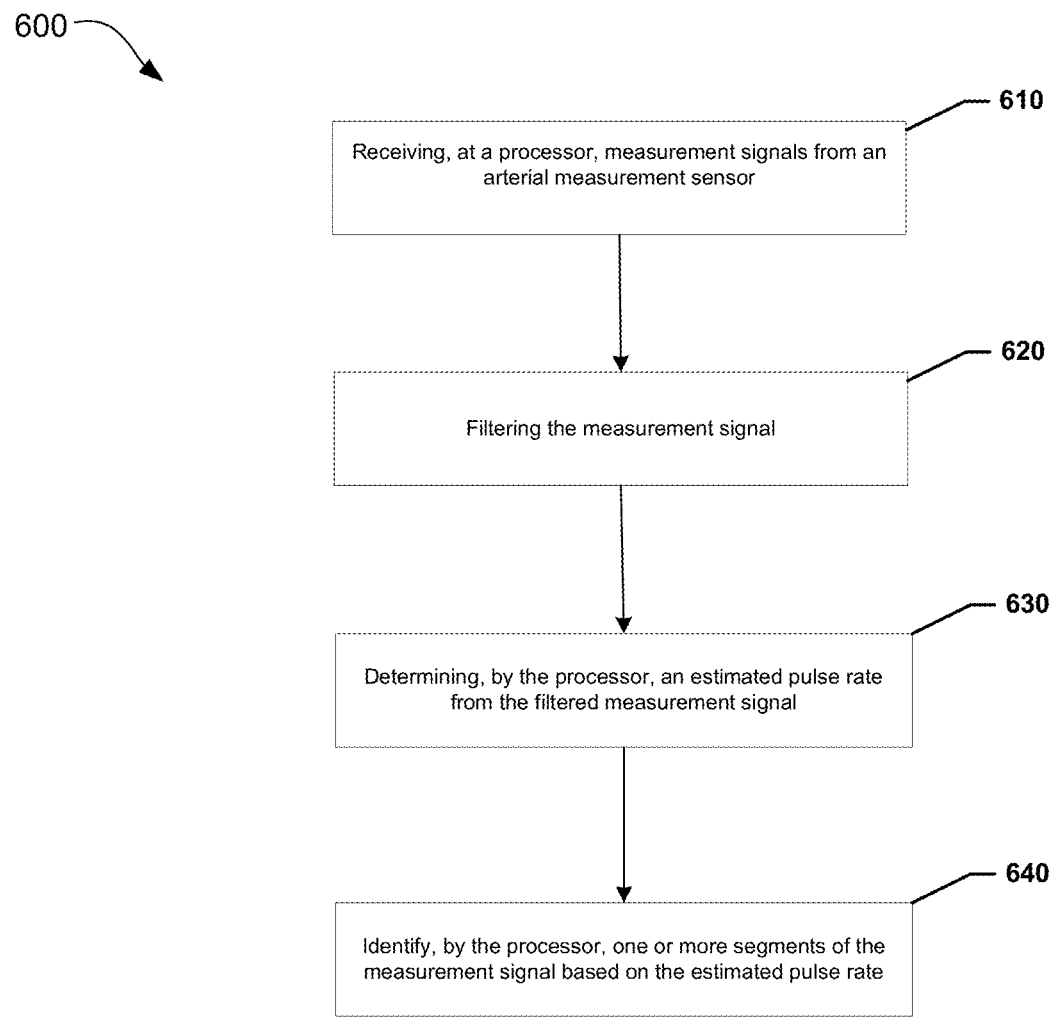
FIG. 6 is a process flow diagram illustrating an embodiment method for identifying one or more segments of the measurement signal.

FIG. 6 illustrates a method 600 of identifying one or more segments of the measurement signal.

In block 610, the one or more processors accesses the measurement signal. In one embodiment, the one or more processors may receive the measurement signals from the measurement sensor directly or indirectly, such as from memory or through one or more intermediate devices.

In block 620, the one or more processors may filter the measurement signal. Examples of types of filters that may be applied to the measurement signals include localization filters, amplitude filters, frequency-based filters, pulse rate filters, or any combination thereof. In one embodiment, the measurement signal may be filtered with one or more filters.

Figure 7:
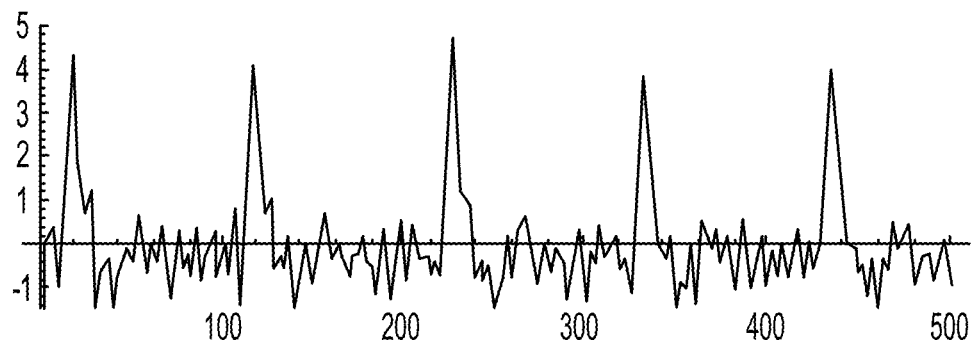
FIG. 7 is a graph of measurement signals filtered using a low-order Gabor wavelet filter to various embodiments.
Figure 8:
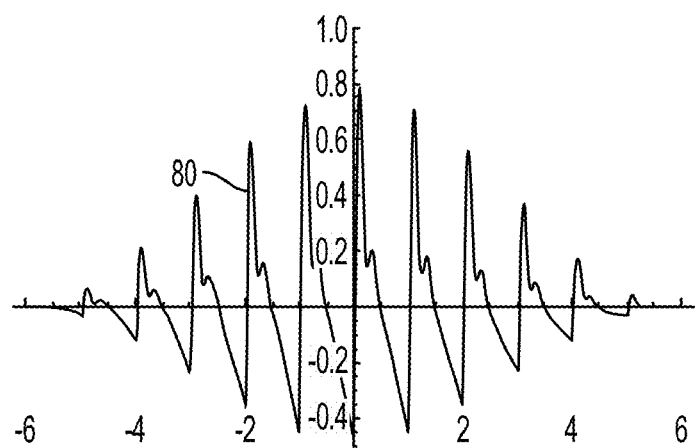
FIG. 8 is a graph of a tailored mother wavelet according to various embodiments.

In one embodiment, the measurement signal may be filtered with one or more wavelets, wherein the wavelet filters may be related to pulse localization in time, amplitude and shape, and periodicity, as described herein with reference to FIGS. 7-8.

As an example, FIG. 7 shows measurement signals filtered using low-order Gabor wavelet filtering.

In one embodiment, the wavelet transform may be a tailored mother wavelet. As an example, FIG. 8 is a graph of a tailored mother wavelet 80 with eight pulses (n=8) on an absolute scale (i.e., the vertical axis) over time (i.e., the horizontal axis). Assuming the measurement signals are high-pass filtered, the mean of the tailored mother wavelet 80 should equal zero. Dilated and contracted versions of the tailored mother wavelet 80 may be correlated with the measured signals by multiplying each dilated/contracted version of the tailored mother wavelet 80 with the measurement signal and subsequently integrating. A predetermined number of scale values may be used, but such a predetermined number may be modified for particular circumstances and/or subjects. The number of pulses of the wavelet will define the number of distension pulses over which averaging is performed.

A mother wavelet $\psi$ may be established from more than one reference pulse, such as a series of previously applied reference pulses, as a superposition of displaced reference pulses. Displaced reference pulses are moved in time (i.e., displaced), but may be otherwise unchanged. In particular, the mother wavelet $\psi$ may represent the sum of displaced reference pulses multiplied by a truncating function defining the number of pulses appearing in the sum. Thus, the mother wavelet $\psi$ may be expressed as:

$$\psi = (\Sigma_n f(t - \tau \times i)) tr(t) \qquad (1).$$

In equation 1, the term "n" is an integer representing the number of pulses being considered, $\tau$ is the separation between pulses and may be set to unity, e.g. 1 sec, i is an integer taking values from 1 to n, and "tr(t)" is a window function that truncates the sequence of pulses. Less than twenty pulses (n<20) may generally be considered assuming a temporal length of the preliminary reference pulse of "one", e.g. 1 sec. The window function may be any function known in the art, such as a Hanning, a Hamming, a Gaussian, a Blackman, or a Tukey window as examples. In various embodiments, the window function tr(t) may be expressed as:

$$tr = (1 + \cos[\pi t/n])/2, \text{ where } -1 < t/n < 1$$

and $$tr = 0, \text{ otherwise} \qquad (2).$$

A window function tr(t) may be multiplied on the pulse sequence selected for the mother wavelet in order to provide a smooth truncation. The window function tr(t) may alternatively be a function selected from a group including a Hann (a.k.a., Hanning), a Hamming, a Gaussian, a Blackman, or a Tukey window function. In particular, the Hann window function has been found to provide desirable results. The width of the window function tr(t) is defined by the number "n." A value of n=1 corresponds to just one pulse in the wavelet. At least two pulses in the wavelet may be used for pulse rate estimation.

The wavelet transform may be expressed as:

$$wt(t, \tau) = \frac{1}{\sqrt{\tau}} \int r(t') \psi\left(\frac{t' - t}{\tau}\right) dt'. \qquad (3)$$

Where r(t) is the measured signal, where a simple pre-filtering may have been applied in order to reduce some high frequency noise and/or a dc-component. The dc-component is the mean off-set relative to zero amplitude. The average pulse length at a given time t may be found as either the peak of the wavelet transform wt(t,τ) or as the first order moment with respect to the time scale τ. The integral of a product of two functions may be used to obtain a maximum value when the two functions are most alike (i.e., when the two functions exhibit the largest correlation). Such a maximum value generally occurs in the various embodiments when the scale τ equals the mean spacing between pulses. The width, defined by n, of the mother wavelet function $\psi$ at the scale τ corresponding to the maximum correlation may provide an average time T corresponding to the average pulse length multiplied by n. A correlation of the two functions may contain a multiplicative oscillating part, which may be eliminated either by averaging over a few oscillations or by applying a complex mother wavelet where an imaginary part is obtained as the Hilbert transform of a real part. The absolute value of the wavelet transform wt(t,τ) may then be used for determining the average pulse length.

Figure 9:
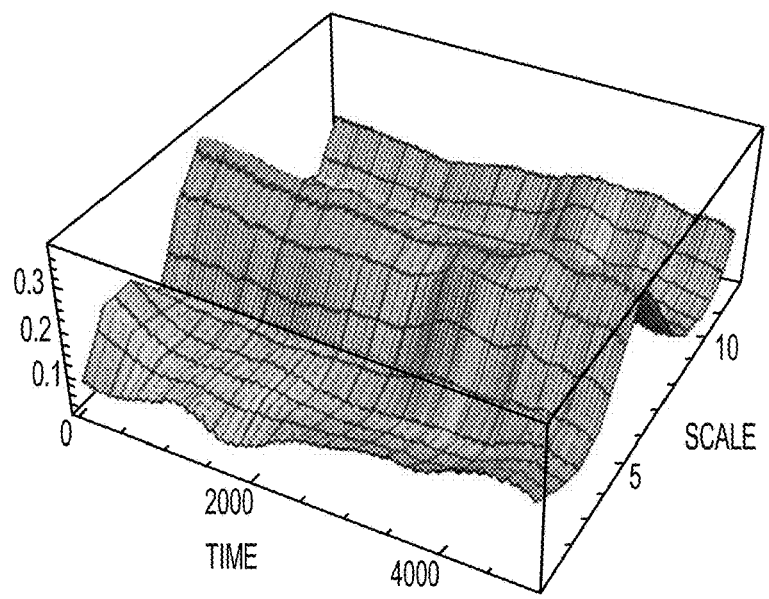
FIG. 9 is a scalogram of measurement signals applied to a wavelet transform according to various embodiments.
Figure 10:
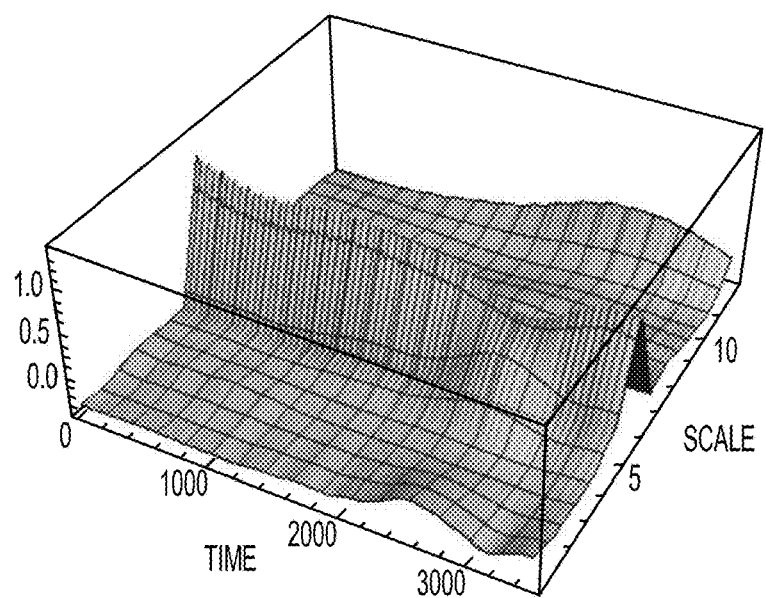
FIG. 10 is another scalogram of measurement signals applied to a wavelet transform according to various embodiments.

As an example, FIGS. 9 and 10 are scalograms illustrating data applied to the wavelet transform wt(t,τ) of equation 3, evaluated at twelve discrete values of the scale τ on the basis of distension measurements performed on a thirty-two year old healthy male subject. A "scalogram" may be used to represent a wavelet transform and may emphasize time scales at different time instances. In FIGS. 9 and 10, the time steps are $1/100^{th}$ of a second (e.g., 1000=10 sec.) and with twelve values of the scale at each time step. FIG. 9 shows a scalogram obtained with a wavelet of three pulses (n=3), while FIG. 10 demonstrates a scalogram obtained with a wavelet of six pulses (n=6). The well-defined ridge of the scalogram defines the pulse rate at any given time "t" averaged over a number of pulses given by the quantity "n". The 3D plots are obtained by evaluating equation 3 at each time step for a number of different scales "τ" (here twelve different values).

Figure 22:
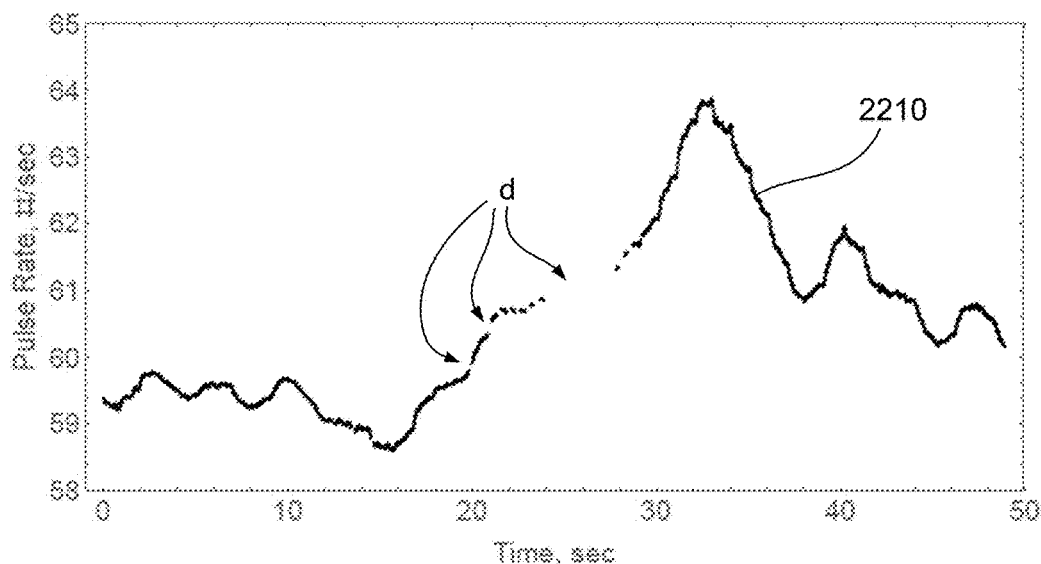
FIG. 22 is graph of estimated pulse rates over time, including drop-outs.
Figure 23:
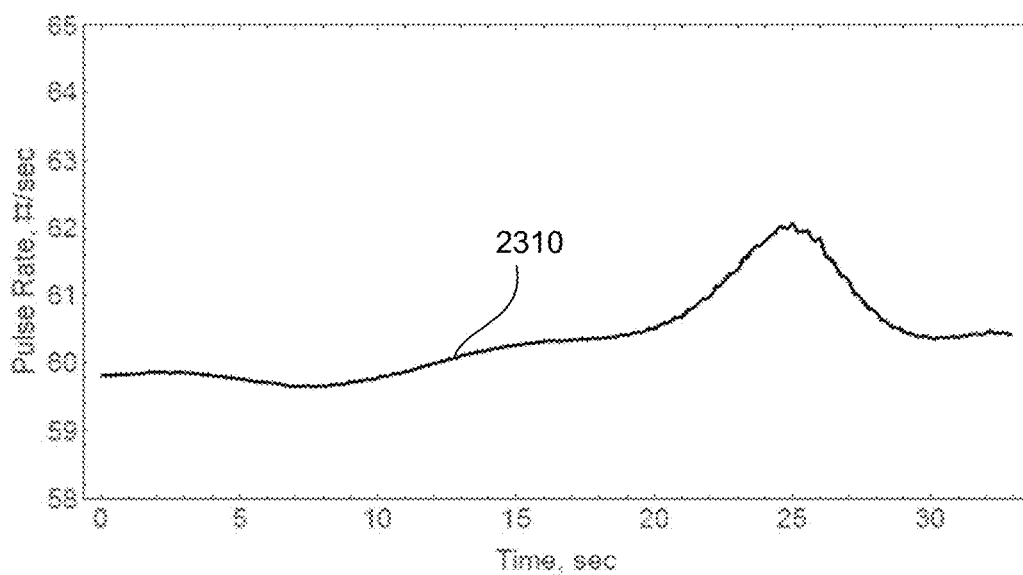
FIG. 23 is graph of estimated pulse rates averaged over a longer time-window than in the graph of FIG. 22.

A processor may evaluate data applied to the wavelet transform wt(t,τ) at different times t and at different time scales τ. Such an evaluation may determine an amplitude change function that reflects the maximum values across the top of the ridge of the scalogram. Each amplitude change function has a different scale τ (an example of such a function is shown in FIG. 22 and FIG. 23). The maximum of each amplitude change function evaluated at a given time t defines the time scale that provides the best match (i.e., correlation) between the measurement signal and the dilated wavelet at the time t of the evaluation. The one or more processors may evaluate data based on one or more different given times t and/or different time scales τ.

Figure 11:
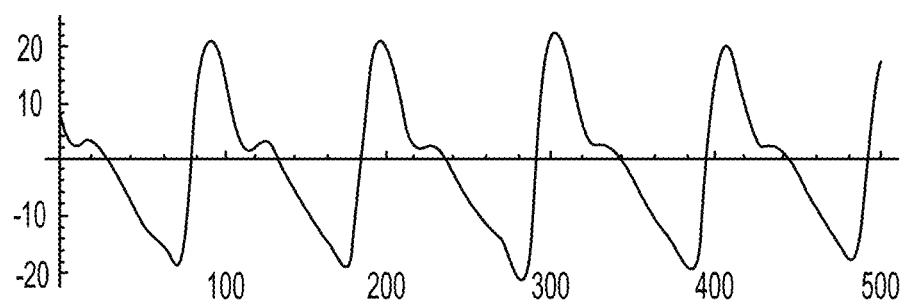
FIG. 11 is a graph of measured pulses to measure amplitude estimates according to various embodiments.

In one embodiment, the measurement signals may be filtered to obtain amplitude and/or pulse shape estimates. As an example, as illustrated in FIG. 11, measurement signals may be filtered using wavelet filtering according to various embodiments to obtain amplitude estimations. In various embodiments, results from an amplitude estimation filtering may be used to determine whether a new reference pulse should be determined, since a significant change in distension amplitude may be caused by the vasomotor. The vasomotor is a region of the medulla of the brain that regulates blood pressure. The vasomotor controls reflex alterations in the heart rate and the diameter of the blood vessels, in response to stimuli from receptors in the circulatory system or from other parts of the brain. Significant changes in distension amplitude as well as pulse shape may also be caused by external and internal stimuli.

Figure 12:
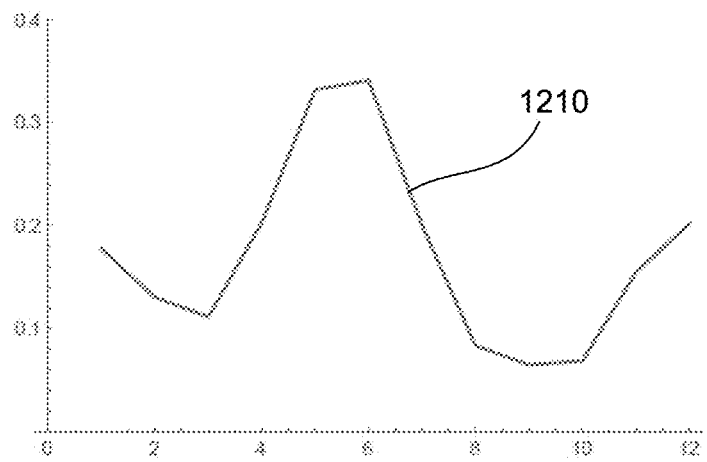
FIG. 12 is a graph of a portion of the scalogram of FIG. 9.
Figure 13:
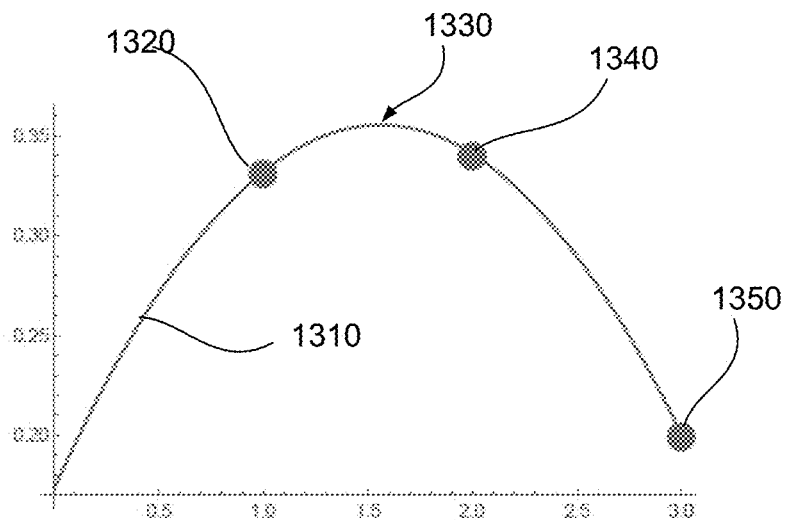
FIG. 13 is a plot of three of the highest values from of the graph of FIG. 13 to which a parabolic curve is fitted.

As an example, FIG. 12 is a graph of an amplitude change function 1210 reflecting changes in amplitude (i.e., vertical axis) evaluated over twelve scales at a fixed time (e.g., 4000 units (40 seconds)) and width (e.g., n=3), from the scalogram of FIG. 9. Each function of scale may be evaluated at a finite number of scales (e.g. twelve values). In order to identify a maximum with a better resolution than the spacing between the different scales, a parabolic fit may be applied to at least three values that surround the maximum, as shown in FIG. 13. The graph in FIG. 12 illustrates the effectiveness of post processing in accordance with various embodiments since the parabolic fit may be used to determine the maximum. Other fitting functions that may be applied include Gaussian or Lorentzian.

As an example, FIG. 13 is a graph of three values 1320, 1340, 1350 extracted as the three largest scale values (i.e., 1-12) from the graph in FIG. 12. By fitting the three values 1320, 1340, 1350 to a parabolic curve 1310, a maximum value 1330 may be extrapolated from the three largest scale values. A Taylor expansion around the maximum for relevant functions provides a quadratic function as a first relevant term, as demonstrated by the parabolic shape of FIG. 13. The maximum value 1330, which may represent the peak of the wavelet transform, may be used to determine a pulse length. This determined pulse length reflects an average over a number of pulses of the mother wavelet. In addition, the reciprocal value of this determined pulse length may correspond to the estimated pulse rate or heart beat rate. The relative resolution of the mother wavelet ψ during the measurement validation may generally be an order of magnitude greater than a reciprocal of the scale values (e.g., 1/12) because of the parabolic interpolation involved.

In one embodiment, the fits are performed at each time increment. Acceptance or rejection of a fit may be based on either the normalized maximum of the fit, which can be no larger than one, may be based on the normalized second derivative of the fit at the maximum, or any combination thereof. This value will in general be slightly below one (unity).

In one embodiment, the temporal locations of the pulses from the measurement signals may be determined based on the onset of each pulse, a systolic maximum amplitude for each pulse, based on a gradient of the pulse, or any combination thereof. For example, the first part of the systolic phase $S_1$, which may generally be characterized by the steepest gradient of an individual pulse may be used to provide a reference location for a pulse (i.e., location estimation). As a further example, the temporal location of a pulse may be estimated from half the amplitude of the onset amplitude and the systolic maximum amplitude. Yet a further example may estimate the temporal location based on where the second order gradient of the pulse is largest, which may yield a location closer to the onset of the pulse.

When filtering for temporal location estimation, it may be desirable to identify the steepest positive gradient in such a way that the likelihood of encountering other similar large gradients within the expected duration of the same pulse becomes negligible. However, while a steep positive gradient may be identified for a particular set of measurement signals (e.g., using filtering for location estimation), the steep positive gradient alone may not necessarily identify the onset of a pulse generated by a heartbeat. Thus, various embodiments may include additional filtering and/or validation techniques for identifying valid pulses that may be applied for measurements.

Figure 14:
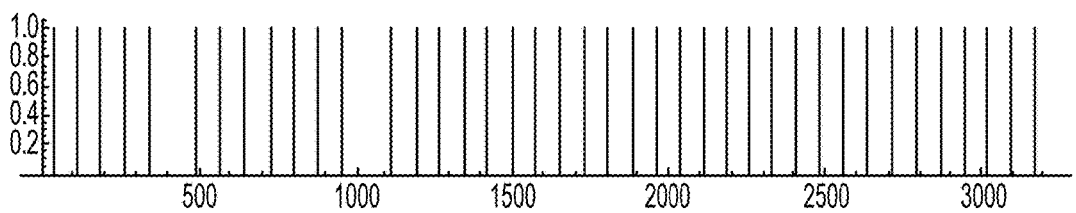
FIG. 14 is a graph of estimated temporal pulse positions according to various embodiments.

FIG. 14 is a graph showing the temporal positions of the filtered and validated pulses for location estimation. For example, the zero-crossings with a positive slope may provide a position in time (i.e., a temporal position) for each pulse. Zero-crossings with a negative slope may be ignored, as well as zero crossings with a positive slope that also include a subsequent zero crossing within a predetermined length of time or a predetermined fraction of the estimated pulse length. For example, the predetermined fraction of the estimated pulse length may be 1/10 or smaller. Other methods for time localization of individual pulses may be used, such as half minimum-maximum locations or features of second order derivatives.

In block 630, the one or more processors may determine an estimated pulse rate of the subject from the filtered measurement signals. In one embodiment, the pulse rate may be determined by identifying the number of peaks in the filtered measurement signals. In one embodiment, the one or more processors may determine an estimate pulse rate based on the one or more reference pulses, an average of previously validated pulses, or any combination thereof. Various embodiments may filter measurement signals from the one or more arterial measurement sensors in order to eliminate at least some of the perturbations that do not match basic characteristics of expected pulse shapes. The cardiovascular system is not a resonant system itself, despite the (quasi-) periodicity of pulses that are typically encountered. Thus, individual pulses within measurement signals may be identified and validated using filtering techniques to accommodate the expected form and variability of pulse shapes. For example, finite impulse response (FIR) filters have been designed on the basis of a solid knowledge about expected pulse shapes and variability of those shapes. In addition, wavelet filters may be applied in order to accommodate conflicting requirements in relation to pulse localization in time and pulse width as well as pulse rate, which corresponds to the classical time-frequency dilemma.

Figure 15:
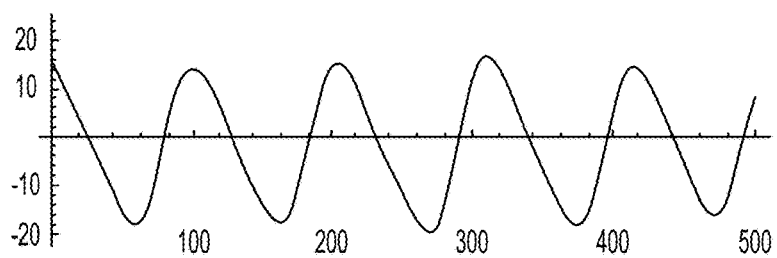
FIG. 15 is a graph of one or more measured pulses filtered for pulse rate estimation according to various embodiments.

As an example, FIG. 15 shows measurement signals filtered using wavelet filtering for pulse rate estimation. The wavelet filtering may use well established wavelet filters and/or a tailored mother wavelet function determined based on a previous validation. Other filtering methods may be used alternatively and/or additionally in accordance with various embodiments.

In one embodiment, the one or more processors may determine two or more pulse location for the measured pulses from the filtered measurement signal and/or the measurement signal. In one embodiment, the estimate pulse rate may be determined from the two or more pulse locations for the measured pulses.

In one embodiment, the estimate pulse rate is compared to one or more pulse rate thresholds. In response to the estimated pulse rate being below one or more pulse rate thresholds then the one or more processors may exit prematurely to conserve power and avoid needless processing. In response to the estimated pulse rate meeting or exceeding one or more pulse rate thresholds then the one or more processors may proceed with the method.

In block 640, the one or more processors may identify one or more segments in the measurement signal. In one embodiment, the one or more processors may identify one or more segments in the measurement signal based on the estimated pulse rate. For example, the one or more processors may isolate one or more segments in the measurement signal that have a similar and/or constant pulse rate. A constant pulse rate may result in more accurate measurement validation, particularly for the measurement validation. Therefore, various embodiments may monitor a pulse rate of initially filtered and/or unfiltered measurement signals until the pulse rate is approximately constant when averaged over at least ten seconds, and typically up to one minute. Once a constant pulse rate is detected, the measurement validation procedure may begin or continue. Variations of pulse durations may be observed from pulse to pulse, but an average pulse duration, the inverse pulse rate, may be constant under steady-state conditions. A steady-state condition is preferable for updating reference pulses based on measured reference pulses.

In one embodiment, the estimated pulse rate may be used to locate pulses in the filtered measurement signals, which may then be compared to one or more reference pulses. A comparison of the located pulses to the reference pulse may provide a correlation for each of the located pulses relative to the reference pulse. The one or more processors may then identify one or more segments in the measurement signal corresponding to one or more measured pulses based on correlation meeting or exceeding a threshold. For example, the one or more processors may locate pulses that deviate from the reference pulse by no more than a predetermined correlation coefficient or maximum deviation and thereby identify one or more segments that contain those pulses.

Figure 16:
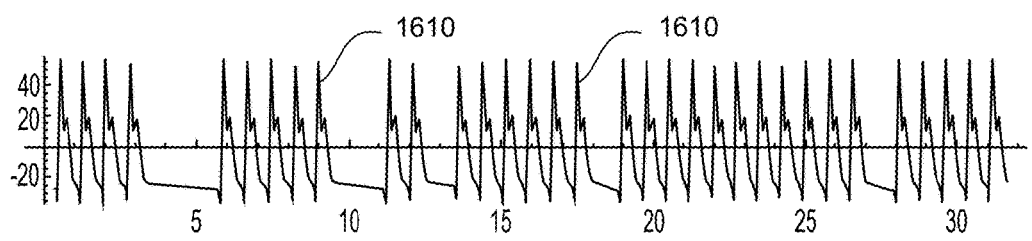
FIG. 16 is a graph of scaled reference pulses substituted in the temporal positions according to various embodiments.

In one embodiment, the reference pulses may be substituted in the temporal positions of select pulses that meet a correlation threshold. As an example, FIG. 16 illustrates select ones of the initially validated pulses normalized to the reference pulse. A processor may normalize each initially validated pulse by substituting a scaled version of the reference pulse for each initially validated pulse. The scale of each normalized initially validated pulse may be based on an individual correlation coefficient that reflects a ratio between the initially validated pulse and the reference pulse. To select the initially validated pulses to normalize, the one or more processors may also apply a correlation threshold that sets a level of correlation required for further validation. Thus, the substituted reference pulses reflect only those scaled reference pulses with a peak normalized correlation meeting the correlation threshold. For example, in FIG. 16 although the individual pulses 1610 may vary in amplitude, those individual pulses represent further validated pulses with a correlation coefficient higher than a correlation threshold. Initially validated pulses that do not meet the correlation threshold may be rejected or excluded from further processing. A processor may use a preset value of 0.7 or higher for the correlation threshold. In addition, a requirement may be established that at least 10% of the initially validated pulses be accepted. Thus, the correlation threshold may include a level of correlation as well as a correlation quota. A higher or a lower level of correlation and/or correlation quota may also be applied.

In accordance with various embodiments, a reference pulse may be used for comparison to the individual pulses to validate select pulses and further eliminate perturbations that deviate significantly from characteristics of the reference pulse. The comparison to the reference pulse may be performed only on individual pulses that passed the initial filtering. The comparison may allow each individual pulse to be further analyzed to ensure that pulse fulfills certain criteria before being accepted for further cardiovascular estimation, such as pulse rate estimation, blood pressure, etc.

Figure 17:
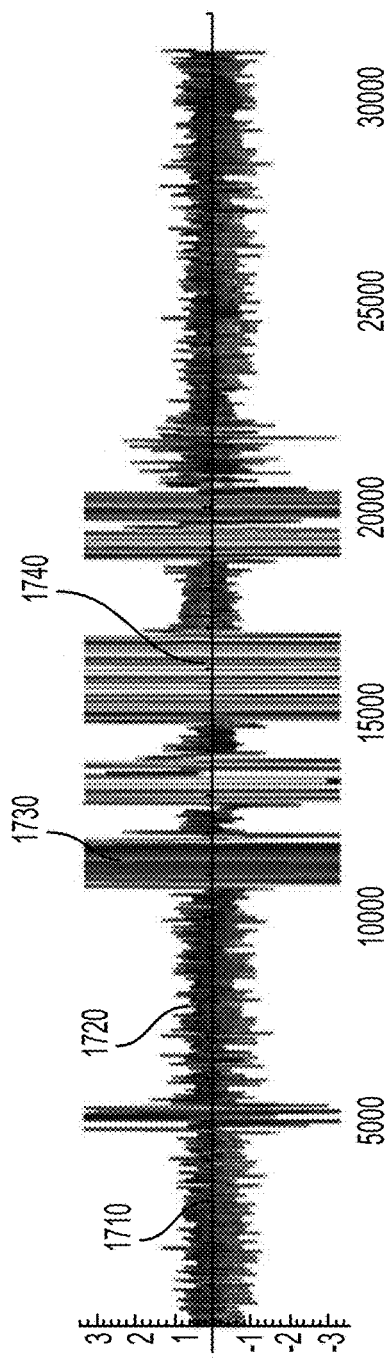
FIG. 17 is a graph of a high-pass measurement signal.

One or more segments of the measurement signal may be determined, because there may be portions of the measurement signal that have significant perturbations. In one example, the erroneous signals may be distinguished easier if their perturbations to the signal are significant compared to small perturbations. As an example, FIG. 17 is a graph of pre-filtered measurement signals (e.g., high-pass filtered), including several significant perturbations from movement on the part of the subject. A first portion 1710 of the measurement signals corresponds to no movement on the part of the subject. After a brief perturbation unrelated to movement by the subject, a second portion 1720 reflects no movement on the part of the subject, but with the subject carrying a 5 kg load. A third portion 1730 shows a perturbation corresponding to the subject bending his arm, at a frequency of 1 Hz, while holding the 5 kg load. The frequency (i.e., 1 Hz) may correspond to a rate at which the subject swings, bends, or twists a limb (e.g., an arm). The frequency of 1 Hz may be used since that frequency typically closely matches the frequency of heartbeats. Periodic movements with a frequency of about 1 Hz may interfere with the pulse measurement signals more than movements at other frequencies. Similarly, a fourth portion 1740 shows another perturbation, but this time corresponding to the subject twisting his hand 180 degrees also with a repetition frequency of 1 Hz.

Figure 18:
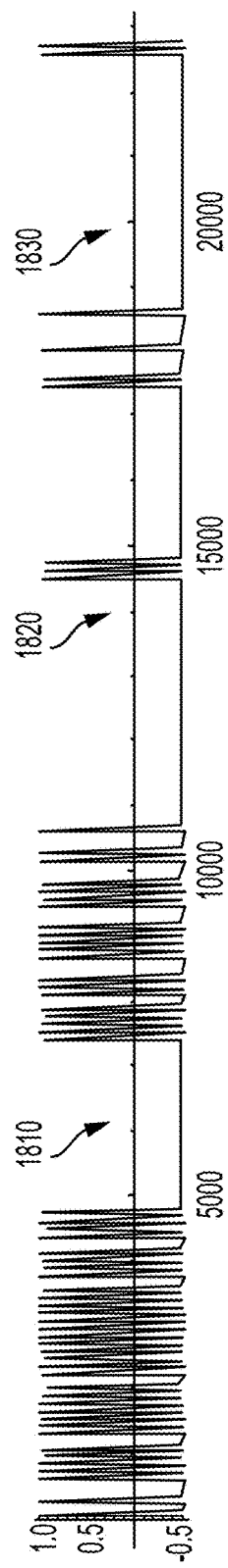
FIG. 18 is a graph of identified one or more segments of the measurement signal according to various embodiments.

As an example, FIG. 18 is a graph of scaled reference pulses located at the positions of initially validated and accepted pulses derived from measurement signals after processing in accordance with various embodiments. The graph starts with a relatively steady set of pulses until the first portion 1810, which corresponds to repetitive arm bending at the subject's heart rate. The first portion 1810 is represented on the graph as a flat line, because in accordance with various embodiments the erratic signals associated with the subject moving are discarded since such pulse measurements at those times may not be accurate measurements of the subject's pulse rate. Similarly, the second portion 1820, corresponding to the subject swinging his arm at about 1 Hz, and the third portion 1830, corresponding to the subject twisting his wrist at about 1 Hz, are flat line regions. In addition to perturbations from movement, other erratic measurement signals may also be discarded in order to identify those pulses that are a better representation of the subject's pulse, and thus better suited for use in calculating the subject's vital signs.

In another example, the one or more segments of the measurement signal may be identified based on steadiness of the estimated pulse rate. For example, if the estimated pulse rate varies over a period of time that meets or exceeds a threshold then the segment associated with the period of time may be separate into smaller segments.

In another example, the one or more segments may be determined based on the number of pulses. For example, one or more segments may be determined based on the estimate pulse rate but if it does not meet the number of pulse threshold then the segment may be merged with a different segment or may be rejected. In another example, a segment may be identified based on the number of pulses meeting or exceeding a number of pulses threshold.

In one embodiment, method 600 may be combined with method 200. For example, method 600 may be used to identify one or more segments of the measurement signal and the one or more measured pulses may be used from the one or more segments of the measurement signal in method 200. This may be used as a filter to avoid needless processing by the measuring device 101 for segments of the measurement signal where there is a low chance of identifying valid pulses.

Figure 19:
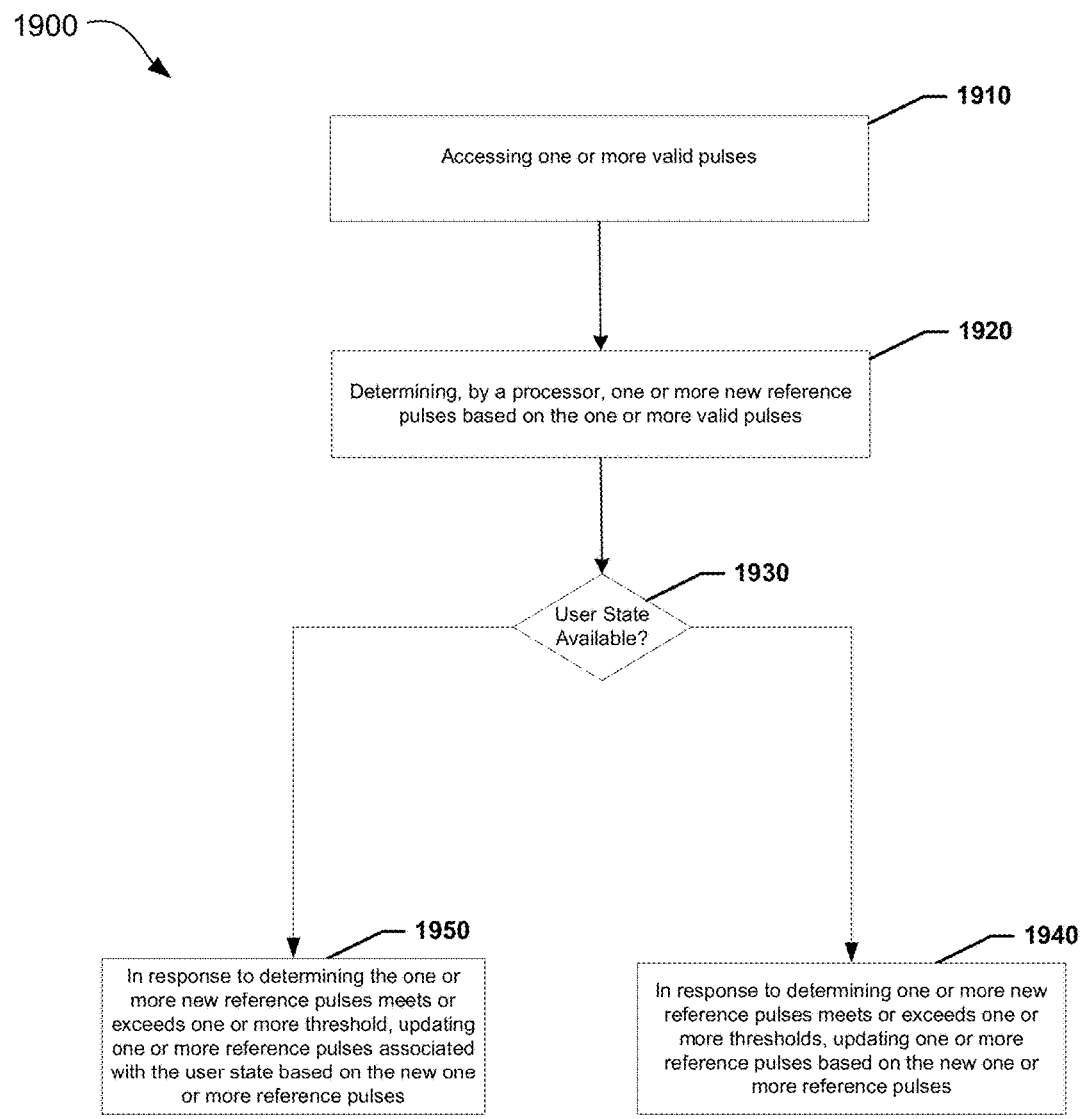
FIG. 19 is a process flow diagram illustrating an embodiment method for determining one or more reference pulses.

FIG. 19 illustrates a method 1900 of updating the reference pulse. In block 1910, the one or more processors may access one or more valid pulses. In one embodiment, the one or more processors may receive the one or more valid pulses.

In one embodiment, the one or more processors may determine an average pulse signal (e.g., pressure) vs. time profile (sometimes referred to herein as a "pulse shape,") of the validated pulses. The one or more processors may perform pulse averaging by scaling and/or temporally aligning (i.e., aligning individual pulses in time) the validated pulse signals (e.g., pressure) vs. time.

Figure 20:
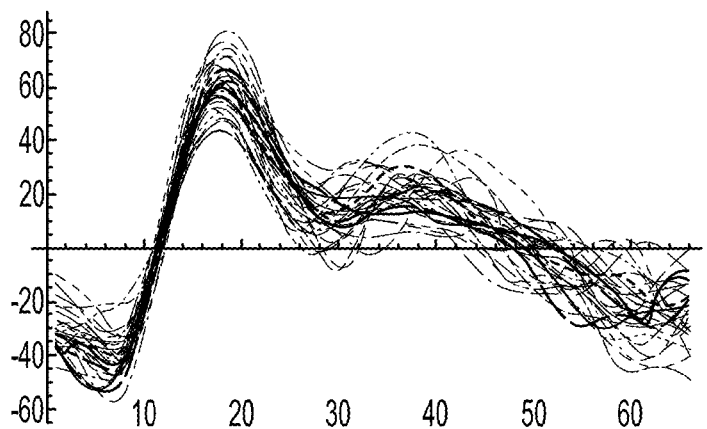
FIG. 20 is a graph of valid pulses temporally aligned with one another for averaging.

As an example, FIG. 20 is a graph of selected measured pulses temporally aligned with one another for averaging. The select measured pulses include those measured pulses that correspond to the initially validated pulses from FIG. 16.

Figure 21:
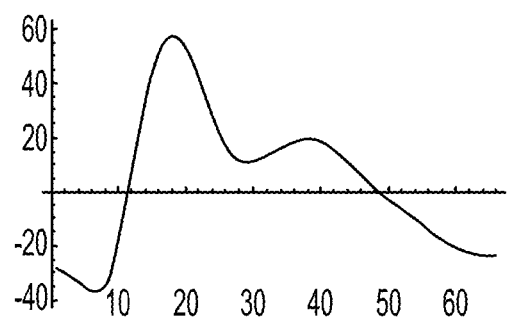
FIG. 21 is a graph of an average reference pulse determined based on averaging the pulses of FIG. 20, according to various embodiments.

As an example, FIG. 21 is a graph of an average pulse obtained by averaging the select measured pulses of FIG. 20. This average pulse may be applied subsequently as a subject-specific reference pulse.

In block 1920, the one or more processors may determine whether to update the one or more reference pulses. In one embodiment, if the peak normalized correlation meets or exceeds one or more reference pulse thresholds, then the one or more reference pulses may be updated. In one embodiment, the one or more reference pulses may be updated based on the number of valid pulses meets or exceeds one or more thresholds. In one embodiment, the one or more reference pulses may be updated based on the averaged validated pulse signals. The average of the validated pulses may be saved in memory representing a subject-specific reference pulse, which may be used subsequently as a reference pulse in method 200. In one embodiment, if the peak normalized correlation meets or exceeds one or more reference pulse thresholds and a subject's state is determined then one or more reference pulses may be associated with the subject's state. For example, if a subject is determined to be in a sleep state, the peak normalized correlation meets the threshold and there are no reference pulses associated with a subject being in a sleep state then the one or more validated pulses may be used to determine one or more sleep reference pulses. In one embodiment, the subject's state may be a sleep state, exercise state, low movement state, or stressed state.

Alternatively, if prior reference data is available for use, including a previously determined subject-specific reference pulse, the reference pulse may be based on such prior reference data. However, without the use of a previously validated reference pulse, a preliminary reference pulse may be defined on the basis of pulse features that are common to most subjects (e.g., illustrated in FIG. 4, FIG. 5A and FIG. 5B). Some elements visible in a pulse shape, such as reflections (R), may not need to be considered since such elements tend to differ considerably from subject to subject. Also, the preliminary reference pulse used for an initial measurement validation may be designated to have a predetermined average pulse length, such as a duration of one second (1 sec.). The predetermined average pulse length of the preliminary reference pulse may be longer or shorter than one second as desired. Alternatively, even though a preliminary reference pulse is used for an initial measurement validation, a prior average pulse length of the subject or a mean pulse length based on age or other biometric characteristics may be used for the preliminary reference pulse. The reference pulse may also incorporate a variable pulse length where the length may be incorporated in the correlation procedure.

Thus, if prior reference data with a subject-specific reference pulse is not available for use, various embodiments may use a generic model for a preliminary reference pulse. For example, a saw-tooth function $f(t)$ may be used, which may be expressed as:

$$f(t) = \begin{cases} 1 - t \text{ if } 0 \leq t \leq 1 \\ 0, \text{ otherwise} \end{cases} \quad (4)$$

Equation 4 may be scaled in time t to match the anticipated pulse rate and may accommodate a likely skewness of pulses. However, since not all pulse features may be represented, another function may be used. For example, a third order function may be used, which may be expressed by its Laplace transform as:

$$F_3(s) = \left(\frac{1}{s^2 + s\xi\omega_0 + \omega_0^2}\right) \frac{1}{s + s\tau}. \quad (5)$$

where quantity s represents an independent variable in Laplace space, the time constant τ represents the diastolic decay time constant and is often comparable to the pulse length (e.g., ~1 sec) (but may be larger or smaller), the parameter $\omega_0$ defines the location of the systolic peak ($1/\omega_0$ is typically about one tenth of the pulse length for younger healthy persons but otherwise may be larger), and the parameter ξ accounts for the oscillatory nature of the pulse. A value of ξ above unity implies no oscillations. A young subject typically has an oscillatory pulse (e.g., FIG. 5A), whereas in older subjects the oscillations may be very small or absent (e.g., FIG. 5B).

A reference pulse may also accommodate the asymptotic value of the diastolic decay that may have a non-negligible value, which may correspond to 40 mmHg and may be expressed as:

$$f(t) = ((1-\exp[-4t/\tau_a]\cos[\omega_a t]) + 2)\exp[-t/\tau_d] - f_m \quad (6).$$

In equation 6, the term, "$\omega_a$" represents the characteristic frequency of the oscillatory part of the pulse times $2\pi$. The term "$\omega_a$" is generally larger than the reciprocal pulse length and may be ten times the pulse length or five times the pulse length or some value in this range. The term "$\tau_a$" represents the decay time constant of the oscillations. For example, in younger subjects, several oscillations may be observed implying that $\tau_a = N/\omega_a$ where N may be 2 or 5 or some value in this range. In another example, for older subjects, the value of N may be smaller than unity. The term "$\tau_d$" represents the decay time constant for a transfer to veins and is typically comparable to the pulse length; and the term "$f_m$" represents a mean pulse value at a given time t averaged over at least one pulse. The terms $\omega_a$, $\tau_a$, $\tau_d$, $f_m$ may be determined based on specific attributes of the subject, such as age, body mass index (BMI), weight, height, and/or gender.

The characteristic frequency of the oscillatory part "$\omega_a$" may be determined based on the location of the dicrotic notch, which may be the first major dip of the pulse after the systolic peak and the subsequent oscillations that may extend into the diastolic phase of the pulse. In one example, taller subjects may have a slightly lower frequency of these oscillations compared to smaller subjects. As an example, the dicrotic notch may be located at a temporal position in the range of ⅙ to ⅓ of a total pulse length, which occurs at about ⅙ to ⅓ of a second after the start of a pulse since the total pulse length may be estimated to be approximately one second.

The decay time constant "$\tau_a$" defines how many oscillations occur within a pulse. As an example, for older subjects, one or no oscillations may be observed implying that $\tau_a \leq 1/\omega_a$. In another example, for younger healthy subjects, the oscillations may appear to be generally more pronounced implying that $\tau_a > 1/\omega_a$. In one example, subjects with a high body mass index (BMI) may have pulses with few oscillations compared to subjects with a lower body mass index. The diastolic decay time constant "$\tau_d$" may typically be on the order of the pulse length. The term "$f_m$" may correspond to a quantity equaling the mean of the first part of the term in equation 5, which is the mean value of: $((1-\exp[-4t/\tau_a]\cos[\omega_a t]) + 2)\exp[-t/\tau_d]$. Subtracting "$f_m$" ensures that the mean of the reference pulse is zero. In one embodiment, if one or more bioimpedance sensors are used, this recognizes that a direct current (DC) part of the signal in general may be removed by high-pass filtering but this may also be used for other waveforms generated by different sensors. For the initial validation measurements and training of the algorithm used for subsequent validation measurements, the specific shape of the preliminary reference pulse may be less critical if the subject is sitting and relaxed as opposed to moving.

Various embodiments may determine an estimated pulse rate using the reference pulse (e.g., equation (6)) as a basis to construct a mother wavelet. The reciprocal value of an average pulse length may define the estimated pulse rate. In order to obtain values of the pulse length averaged over a number of pulses, which may include at least two pulses but typically six pulses or more, various embodiments may apply a wavelet transform with a mother wavelet in order to estimate the pulse rate. A wavelet transform refers to a mathematical operation used to divide another function or continuous-time signal into different scale components.

FIGS. 22 and 23 are graphs of two different estimated pulse rates 2210, 2310. In FIG. 22, the temporal resolution is three seconds on the basis of a fifty-second record of distensions. The graph in FIG. 22 shows changes in the estimated pulse rate 2210 over time that includes drop-outs d. The drops-outs d may correspond to measurement signals rejected by validation procedures of various embodiments. Measurement signals may be rejected when the quality does not meet predetermined standards for estimating pulse rate. For example, measurement signals may be rejected due to inadequate quality at particular times. The graph in FIG. 23 shows changes in the estimated pulse rate 2310 over time that includes a temporal resolution of six seconds (i.e., a longer time-window) on the basis of the same record of distensions used for the graph of FIG. 22. FIGS. 22 and 23 illustrate the trade-off between temporal resolution and acceptance of estimates. Various embodiments adapt the estimated pulse rate to a current state of the subject. The time window for pulse rate estimation may also be set according to a desired temporal or spectral window for estimating pulse rate variability. The shortest time scale for the window could be given by the number of pulses of the mother wavelet and a larger time scale such as 10 second or larger may be selected for the longest time scale. A Fourier analysis of pulse rate fluctuations may also be performed.

The preliminary reference pulse may be updated to reflect a new subject-specific reference pulse using the average reference pulse determined at the conclusion of the initial measurement validation in place of the preliminary reference pulse. Alternatively, a previous subject-specific reference pulse may be updated to reflect a new subject specific reference pulse. A refined correlation threshold, more stringent than the initial correlation threshold, may be used. For example, a processor may use a preset value of 0.9 as the refined correlation threshold. Alternatively, a higher or lower preset value may be used as the refined correlation threshold. If a significant change in the distension amplitude is observed a new reference pulse may be established as described above.

The peak normalized correlation may compare each measured pulse to the reference pulse using the determined location of each pulse. Each individual pulse may be substituted by the reference pulse scaled by a correlation coefficient. The correlation coefficient may be calculated based on a difference between the analyzed individual pulse and the reference pulse. The correlated pulses may consist of a series of pulses similar to the reference pulse but differing in scale by varied correlation coefficients.

The validation methods of various embodiments may be implemented with one of several signal and data processing devices such as a Digital Signal Processing device, a Mixed Signal Processing ASIC, an FPGA, microprocessor, microcontroller or a dedicated implementation based on a combination of analog and/or digital components.

Figure 24:
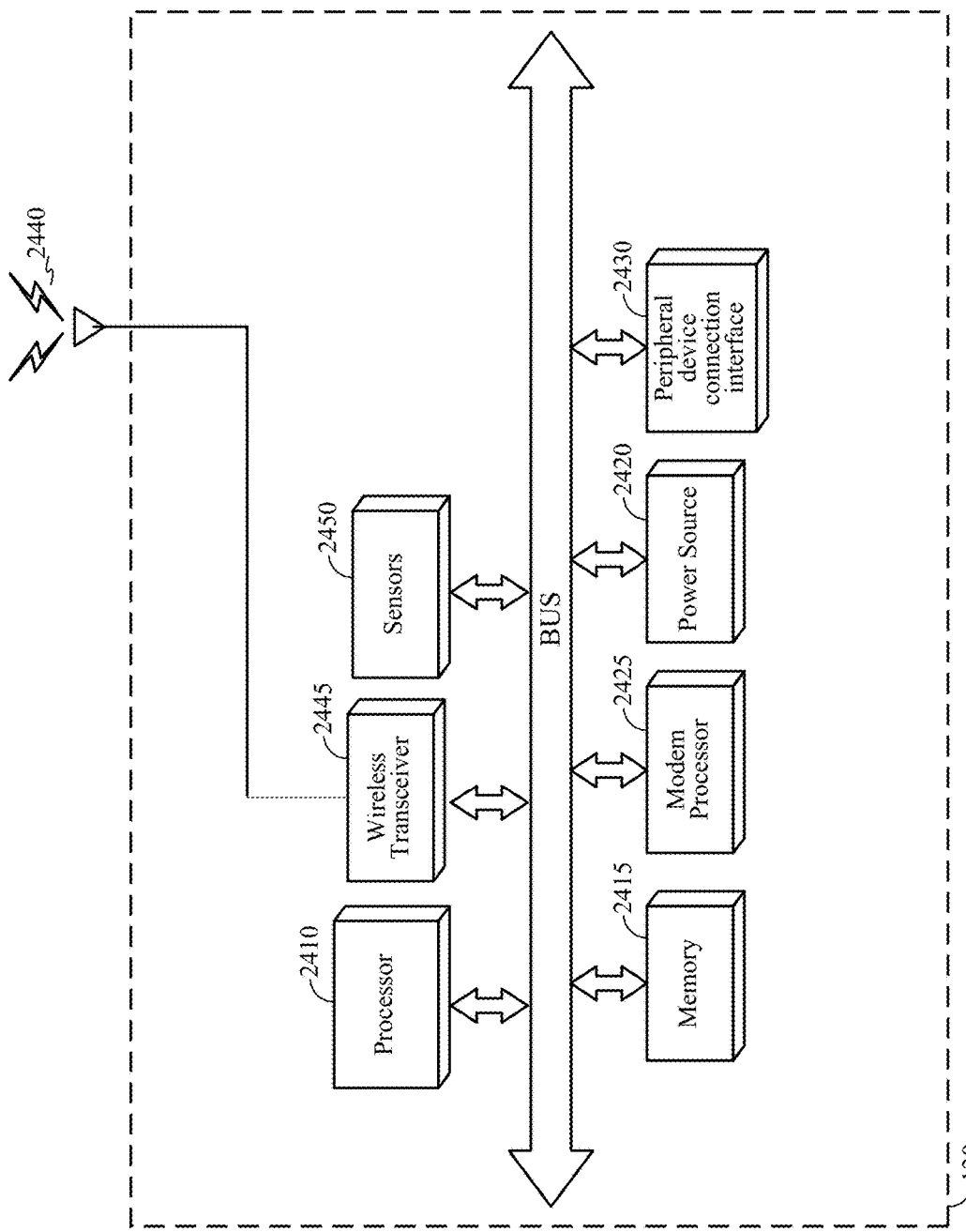
FIG. 24 is a component block diagram of a control unit in the form of a computing device according to various embodiments.

An embodiment measuring device may be configured to transmit data to any of a variety of computing devices. For example, FIG. 24 illustrates a computing device 130 suitable for use in various embodiments. The computing device 130 may exchange data to and/or from the measuring devices discussed above, such as the sleeve 110, and may perform one or more of the operations of method 200, 600, and/or 1900 described above. For example, several quantities related to arterial pressure and/or measured pulses, hydrostatic pressure, and/or elevation of a sensor (and/or device) may be sent from the measuring device to the computing device 130. The blood pressure related quantities may be the Systolic Blood Pressure (SBP), which is the maximum arterial pressure represented by the peaks of the pressure pulses, it may be the Diastolic Blood Pressure (DBP), which is the minimum arterial pressure represented by the minimum values of pressure pulses, or it may be the Mean Arterial Pressure (MAP). The Pulse Pressure (PP or δp) is the difference between SBP and DBP.

The term "computing device" is used herein to refer to any one or all of cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and configured to communicate with a measuring device described herein, such as a negligible interfering and negligible perception configuration or form measuring device (e.g., a wearable patch, bracelet, anklet, watch, etc.).

In various embodiments, the computing device 130 may include a processor 2410 coupled to a memory 2415. The processor 2410 may be one or more multicore ICs designated for general or specific processing tasks. The memory 2415 may be volatile or non-volatile memory, and may also be secure and/or encrypted memory, or unsecure and/or unencrypted memory, or any combination thereof.

The computing device 130 may have one or more radio signal transceivers 2445 (e.g., WLAN, RF, cellular, near field, Bluetooth®, GNSS etc.) and one or more antennae 2440, for sending and receiving, coupled to each other and/or to the processor 2410. The transceivers 2445 and one or more antennae 2440 may be used with the above-mentioned circuitry to implement the various wireless transmission protocol stacks and interfaces. The computing device 130 may include one or more modem processors 2425 coupled to the one or more processors. The one or more modem processors enable communication via a wide area network, local area network, personal area network, near field, etc. The one or more modem processors may also include reception of signals from global navigation satellite systems (GNSS).

The computing device 130 may include a peripheral device connection interface 2430 coupled to the processor 2410. The peripheral device connection interface 2430 may be singularly configured to accept one type of connection, or multiply configured to accept various types of physical and communication connections, common or proprietary, such as USB, FireWire, Thunderbolt, or PCIe. The peripheral device connection interface 2430 may also be coupled to a similarly configured peripheral device connection port (not shown). The computing device 130 may include a power source 2420 coupled to the processor 2410, such as a disposable or rechargeable battery. The rechargeable battery may also be coupled to the peripheral device connection port to receive a charging current from a source external to the computing device 130.

The computing device 130 may include one or more sensors 2450. The one or more sensors may include one or more cameras, one or more accelerometers, one or more gyroscopes, one or more magnetometers, one or more barometers, one or more ambient light sensors, one or more ultrasound sensors, one or more PPG sensors, one or more IPG sensors, one or more pressure sensors, one or more chemical sensors, one or more biosensors, one or more temperature sensors, one or more humidity sensors, one or more acoustic sensors or any combination thereof.

Processors of computing devices suitable for use in various embodiments may be any programmable microprocessor, microcontroller, microcomputer or multiple processor chip or chips that can be configured by processor executable instructions (e.g., applications or software) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store applications and/or software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors. The processors may be a means for performing methods 200, 600, 1900 or any combination thereof.

The above description has mainly addressed different embodiment methods, systems, and devices for identifying valid measurements from an artery in a limb of a subject with a non-interfering continuous measuring device. Various embodiment methods may start by providing a reference pulse and performing a measurement validation. In response to completing a measurement validation, various embodiment methods may adjust the reference pulse to take into prior measurements of the subject. The measurement device may thus provide continuous measurements using a series of adjusted reference pulses each updated from previous measurement/validation cycles.

In some embodiments, the device may be attached to the subject without any initial measurement validation being performed. In some embodiments, the device may use previous measurements to adjust and/or update the measurement validation. In some embodiments, if not enough data points are collected to accurately identify valid measurements, one or more of the various method operations described above may be performed or repeated.

In various embodiments, the measuring device may be programmed with a measurement validation or with an initial set of parameters, which are statistically close to a large number of subjects. This initial "rough" measurement validation may then be adapted via adaptation algorithms over time. In another embodiment, the initial "rough" measurement validation may be determined by matching a number of physical parameters of the subject to a database of test subjects and choosing the parameters of the test subject that are closest to the subject.

The foregoing method descriptions and the process flow diagrams are provided merely as illustrative examples and are not intended to require or imply that the operations of various embodiments must be performed in the order presented. As will be appreciated by one skilled in the art, the order of operations in the foregoing embodiments may be performed in more than one order. Words such as "thereafter," "then," "next," etc. are not intended to limit the order of the operations; these words are simply used to guide the reader through the description of the methods. Further, any reference to claim elements in the singular, for example, using the articles "a," "an," or "the" is not to be construed as limiting the element to the singular.

While the terms "first" and "second" are used herein, for example to describe electrodes or other elements, such identifiers are merely for convenience and are not meant to limit various embodiments to a particular order, sequence, type of network or carrier.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the one or more processors may be any conventional processor, controller, microcontroller, state machine or any combination thereof. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Various embodiments include methods, devices, and systems for identifying valid pulses obtained with a pulse measuring device positioned on a limb of a subject performing measurements of arterial dynamics. The methods, devices, and systems of various embodiments may identify relevant pulses and pulse sequences for more a reliable estimate of cardiovascular quantities, such as blood pressure. Devices in accordance with various embodiments may be incorporated into articles worn by a subject or remaining in contact with the subject for continuous validation over extended periods. In addition, the devices in accordance with various embodiments may avoid interference with the arterial measurements being taken.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method of identifying valid pulses from one or more measured pulses obtained with a measuring device positioned on a subject's body, wherein the measuring device performs measurements of arterial dynamics, the method comprising:

accessing, by a processor, sensor data representing the one or more measured pulses from one or more arterial measurement sensors of the measuring device;

determining, by the processor, an estimated pulse rate based on the one or more measured pulses and a first wavelet transform;

identifying, by the processor, at least one measured pulse from the one or more measured pulses within the sensor data based on the estimated pulse rate;

determining, by the processor, whether the identified at least one measured pulse includes one or more valid pulses based on a comparison of one or more first pulse characteristics of the identified at least one measured pulse to one or more second pulse characteristics of one or more reference pulses comprising the one or more valid pulses, wherein the one or more first pulse characteristics are determined based on the identified at least one measured pulse and a second wavelet transform, and wherein the second wavelet transform is determined based on the one or more reference pulses; and based on determining that the identified at least one measured pulse includes one or more valid pulses, outputting, by the processor, a vital sign measurement result of the subject's body computed using a first part of the identified at least one measured pulse that includes the one or more valid pulses and not using a second part of the identified at least one measured pulse that does not include the one or more valid pulses.

2. The method of claim 1, wherein the one or more reference pulses are determined based on age of the subject, body mass index of the subject, weight of the subject, height of the subject, gender of the subject, a state of the subject or any combination thereof.

3. The method of claim 2, wherein the state of a subject comprises a sleep state, a stressed state, a happy state, a depressed state, an exercise state, or a low movement state.

4. The method of claim 1, wherein the one or more reference pulses are determined based on previously validated pulses.

5. The method of claim 1, wherein the accessing, by the processor, the one or more measured pulses from one or more arterial measurement sensors comprises:
   determining one or more segments of measurement signals based on time localization, amplitude, pulse rate, or any combination thereof; and
   identifying the one or more measured pulses based on the one or more segments of measurement signals.

6. The method of claim 1, wherein determining, by the processor, whether the at least one measured pulse includes one or more valid pulses comprises:
   determining, by the processor, one or more peak normalized correlation of the at least one measured pulse based on the one or more first pulse characteristics and the one or more reference pulses; and
   identifying, by the processor, the one or more valid pulses based on a comparison of the one or more peak normalized correlation of the at least one measured pulse and one or more correlation thresholds.

7. The method of claim 6, wherein the one or more first pulse characteristics comprises one or more locations of the one or more measured pulses, one or more pulse shapes of the one or more measured pulses, one or more pulse lengths of the one or more measured pulses, one or more amplitudes of the one or more measured pulses, or any combination thereof.

8. The method of claim 1, further comprising:
   identifying, by the processor, the one or more valid pulses from the first part of the identified at least one measured pulse; and
   in response to the identified one or more valid pulses meeting or exceeding one or more thresholds, determining, by the processor, one or more new reference pulses based on the one or more identified valid pulses or updating, by the processor, the one or more reference pulses based on the one or more identified valid pulses.

9. The method of claim 1, wherein at least one of the first wavelet transform or the second wavelet transform is based on a tailored mother wavelet.

10. The method of claim 9, wherein the tailored mother wavelet represents a sum of displaced reference pulses multiplied by a truncating function defining a number of pulses appearing in the sum of displaced reference pulses.

11. The method of claim 1, wherein the one or more reference pulses are determined based on a first model representing a stroke volume versus time and a second model representing a propagation of a pulse through an arterial system.

12. The method of claim 1, wherein the one or more reference pulses are determined based on previous measured pulses obtained with the measuring device positioned on the subject's body, the previous measured pulses being determined to include the one or more valid pulses.

13. The method of claim 1, wherein the first wavelet transform is determined based on the one or more reference pulses.

14. A measuring device, comprising:
   one or more arterial measurement sensors configured to measure arterial dynamics from an artery when positioned on a subject's body; and
   one or more processors coupled to the one or more arterial measurement sensors, the one or more processors capable of:
      accessing one or more measured pulses from the one or more arterial measurement sensors;
      determining an estimated pulse rate based on the one or more measured pulses and a first wavelet transform;
      identifying at least one measured pulse from the one or more measured pulses based on the estimated pulse rate;
      determining whether the identified at least one measured pulse includes one or more valid pulses based on a comparison of one or more first pulse characteristics of the identified at least one measured pulse to one or more second pulse characteristics of one or more reference pulses comprising the one or more valid pulses, wherein the one or more first pulse characteristics are determined based on the identified at least one measured pulse and a second wavelet transform, and wherein the second wavelet transform is determined based on the one or more reference pulses; and
      based on determining that the identified at least one measured pulse includes one or more valid pulses, outputting, by the one or more processors, a vital sign measurement result of the subject's body computed using a first part of the identified at least one measured pulse that includes the one or more valid pulses and not using a second part of the identified at least one measured pulse that does not include the one or more valid pulses.

15. The measuring device of claim 14, wherein the one or more reference pulses are determined based on age of the subject, body mass index of the subject, weight of the subject, height of the subject, gender of the subject, a state of the subject or any combination thereof.

16. The measuring device of claim 15, wherein the state of a subject comprises a sleep state, a stressed state, a happy state, a depressed state, an exercise state, or a low movement state.

17. The measuring device of claim 14, wherein the one or more reference pulses are determined based on previously validated pulses.

18. The measuring device of claim 14, wherein the accessing the one or more measured pulses from the one or more arterial measurement sensors comprises:
   determining one or more segments of measurement signals based on time localization, amplitude, pulse rate, or any combination thereof; and
   identifying the one or more measured pulses based on the one or more segments of measurement signals.

19. The measuring device of claim 14, wherein determining whether the at least one measured pulse include one or more valid pulses comprises:
   determining one or more peak normalized correlation of the at least one measured pulse based on the one or more first pulse characteristics and the one or more second pulse characteristics; and
   identifying the one or more valid pulses based on a comparison of the one or more peak normalized correlation of the at least one measured pulse and one or more correlation thresholds.

20. The measuring device of claim 19, wherein the one or more first pulse characteristics comprises one or more locations of the one or more measured pulses, one or more pulse shapes of the one or more measured pulses, one or more pulse lengths of the one or more measured pulses, one or more amplitudes of the one or more measured pulses, or any combination thereof.

21. The measuring device of claim 14, the one or more processors further capable of:
    identifying the one or more valid pulses from the first part of the identified at least one measured pulse; and
    in response to the identified one or more valid pulses meeting or exceeding one or more thresholds, determining one or more new reference pulses based on the one or more identified valid pulses or updating the one or more reference pulses based on the one or more identified valid pulses.

22. The measuring device of claim 14, wherein the wavelet transform is based on a tailored mother wavelet.

23. The measuring device of claim 22, wherein the mother wavelet represents a sum of displaced reference pulses multiplied by a truncating function defining a number of pulses appearing in the sum of displaced reference pulses.

24. A measuring device, comprising:
    means for accessing one or more measured pulses from one or more arterial measurement sensors;
    means for determining an estimated pulse rate based on the one or more measured pulses and a first wavelet transform;
    means for identifying at least one measured pulse from the one or more measured pulses based on the estimated pulse rate;
    means for determining whether the identified at least one measured pulse includes one or more valid pulses based on a comparison of one or more first pulse characteristics of the identified at least one measured pulse to one or more second pulse characteristics of one or more reference pulses comprising the one or more valid pulses, wherein the one or more first pulse characteristics are determined based on the identified at least one measured pulse and a second wavelet transform, and wherein the second wavelet transform is determined based on the one or more reference pulses; and
    means for, based on determining that the identified at least one measured pulse includes one or more valid pulses, outputting a vital sign measurement result of the subject's body computed using a first part of the identified at least one measured pulse that includes the one or more valid pulses and not using a second part of the identified at least one measured pulse that does not include the one or more valid pulses.

25. The measuring device of claim 24, wherein the one or more reference pulses are determined based on age of the subject, body mass index of the subject, weight of the subject, height of the subject, gender of the subject, a state of the subject or any combination thereof; and
    wherein the state of a subject comprises a sleep state, a stressed state, a happy state, a depressed state, an exercise state, or a low movement state.

26. The measuring device of claim 24, wherein the one or more reference pulses are determined based on previously validated pulses.

27. The measuring device of claim 24, wherein the means for accessing the one or more measured pulses from the one or more arterial measurement sensors comprises:
    means for determining one or more segments of measurement signals based on time localization, amplitude, pulse rate, or any combination thereof; and
    means for identifying the one or more measured pulses based on the one or more segments of measurement signals.

28. The measuring device of claim 24, wherein the means for determining whether the identified at least one measured pulse includes one or more valid pulses comprises:
    means for determining one or more peak normalized correlation of the identified at least one measured pulse based on the one or more first pulse characteristics and the one or more second pulse characteristics; and
    means for identifying the one or more valid pulses based on a comparison of the one or more peak normalized correlation of the identified at least one measured pulse and one or more correlation thresholds.

29. A non-transitory computer-readable medium for identifying valid pulses, comprising:
    at least one instruction to access one or more measured pulses from one or more arterial measurement sensors;
    at least one instruction to determine an estimated pulse rate based on the one or more measured pulses and a first wavelet transform;
    at least one instruction to locate one or more of the measured pulses based on the estimated pulse rate;
    at least one instruction to determine whether the identified at least one measured pulse includes one or more valid pulses based on a comparison of one or more first pulse characteristics of the identified at least one measured pulse to one or more second pulse characteristics of one or more reference pulses comprising the one or more valid pulses, wherein the one or more first pulse characteristics are determined based on the identified at least one measured pulse and a second wavelet transform, and wherein the second wavelet transform is determined based on the one or more reference pulses; and
    at least one instruction to, based on determining that the identified at least one measured pulse includes one or more valid pulses, outputting a vital sign measurement result of the subject's body computed using a first part of the identified at least one measured pulse that includes the one or more valid pulses and not using a second part of the identified at least one measured pulse that does not include the one or more valid pulses.

30. The non-transitory computer-readable medium of claim 29, wherein the at least one instruction to determine whether the one or more measured pulses include one or more valid pulses comprises:
    at least one instruction to determine one or more peak normalized correlation of the one or more measured pulses based on the one or more first pulse characteristics and the one or more second pulse characteristics; and
    at least one instruction to identify the one or more valid pulses based on a comparison of the one or more peak normalized correlation of the identified at least one measured pulse and one or more correlation thresholds.

* * * * *